US010611987B2

(12) United States Patent
Panandiker et al.

(10) Patent No.: US 10,611,987 B2
(45) Date of Patent: Apr. 7, 2020

(54) ANTIFOAM MOLECULES CONTAINING A SILICA MOIETY AND COMPOSITIONS

(71) Applicant: The Procter & Gamble Company, Cincinnati, OH (US)

(72) Inventors: Rajan Keshav Panandiker, West Chester, OH (US); Bernard William Kluesener, Harrison, OH (US); Rachel Morgan Clayton Roeder, Mason, OH (US); Rebecca Ann Langevin, Norwood, OH (US); Rafael Trujillo, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 229 days.

(21) Appl. No.: 15/421,452

(22) Filed: Feb. 1, 2017

(65) Prior Publication Data
US 2017/0218307 A1 Aug. 3, 2017

Related U.S. Application Data

(60) Provisional application No. 62/289,986, filed on Feb. 2, 2016.

(51) Int. Cl.
| | | |
|---|---|---|
| *C11D 9/36* | (2006.01) | |
| *C11D 3/37* | (2006.01) | |
| *C08G 77/18* | (2006.01) | |
| *C11D 3/00* | (2006.01) | |
| *B01D 19/04* | (2006.01) | |
| *C07C 211/09* | (2006.01) | |
| *C07F 7/04* | (2006.01) | |
| *C08G 77/00* | (2006.01) | |

(52) U.S. Cl.
CPC ........ *C11D 3/3742* (2013.01); *B01D 19/0409* (2013.01); *C07C 211/09* (2013.01); *C07F 7/04* (2013.01); *C08G 77/18* (2013.01); *C11D 3/0026* (2013.01); *C11D 3/373* (2013.01); *C08G 77/70* (2013.01); *C08G 77/80* (2013.01)

(58) Field of Classification Search
CPC .... C11D 9/36; C11D 1/62; C11D 1/82; C11D 3/001; C11D 3/124; C11D 3/3738
See application file for complete search history.

(56) References Cited

U.S. PATENT DOCUMENTS

| | | | |
|---|---|---|---|
| 2,220,099 A | 11/1940 | Guenther et al. | |
| 2,477,383 A | 7/1949 | Lewis | |
| 5,352,604 A | 10/1994 | Wilson et al. | |
| 6,022,724 A | 2/2000 | Svendsen et al. | |
| 6,093,562 A | 7/2000 | Bisgard-Frantzen et al. | |
| 6,521,587 B1* | 2/2003 | L'Hostis ............ | B01D 19/0404 510/347 |
| 6,673,890 B1 | 1/2004 | Boeckh et al. | |
| 7,141,403 B2 | 11/2006 | Outtrup et al. | |
| 8,153,574 B2 | 4/2012 | Boutique et al. | |
| 2008/0193999 A1 | 8/2008 | Andersen et al. | |
| 2010/0093598 A1* | 4/2010 | Davio ................... | A61K 8/062 510/466 |
| 2014/0100293 A1* | 4/2014 | Ando ................. | B01D 19/0409 516/118 |
| 2014/0113851 A1 | 4/2014 | Panandiker et al. | |
| 2014/0121149 A1 | 5/2014 | Panandiker et al. | |
| 2014/0316015 A1* | 10/2014 | Burger ................... | C08L 83/04 516/117 |
| 2014/0352076 A1* | 12/2014 | Song .................... | C11D 3/0026 8/137 |
| 2014/0364515 A1* | 12/2014 | Zeng .................. | B01D 19/0409 516/55 |
| 2015/0119509 A1* | 4/2015 | Brehm ............... | B01D 19/0409 524/147 |
| 2015/0240189 A1 | 8/2015 | Panandiker et al. | |
| 2015/0322380 A1 | 11/2015 | Li et al. | |
| 2016/0017261 A1* | 1/2016 | Bautista Cid ........ | C11D 3/3742 8/137 |

FOREIGN PATENT DOCUMENTS

| | | |
|---|---|---|
| WO | WO 96/02643 A1 | 2/1996 |
| WO | WO 00/60060 A2 | 10/2000 |
| WO | WO 2009/043709 A1 | 4/2009 |
| WO | WO 2009/149130 A2 | 12/2009 |

OTHER PUBLICATIONS

U.S. Appl. No. 15/421,453, filed Feb. 1, 2017, Panandiker, et al.
International Search Report; International Application No. PCT/US2017/015918; dated Apr. 26, 2017; 13 pages.
International Search Report; International Application No. PCT/US2017/015919; dated May 15, 2017; 14 pages.
Brooke, D.N., et al.; Octanol: Water Partition Coefficients (P): Measurement, Estimation, and Interpretation, Particularly for Chemicals with $P>10^5$ [1]; Ecotoxicology and Environmental Safety; 1986; pp. 251-260; vol. 11; No. 3.
Adam, Waldemar, et al; Thianthrene 5-Oxide as a Mechanistic Probe for Assessing the Electronic Character of Oxygen-Transfer Agents; Journal of the American Chemical Society; 1991; pp. 6202-6208; vol. 113; No. 16.

* cited by examiner

*Primary Examiner* — Charles I Boyer
(74) *Attorney, Agent, or Firm* — Andres E. Velarde; James F. McBride

(57) ABSTRACT

The present application relates to cleaning and treatment compositions comprising a material that reduces foam and methods of making and using such material and compositions. Such compositions comprise benefit agents that typically impact the performance of antifoams yet in the present compositions antifoaming properties of antifoams are maintained.

15 Claims, No Drawings

US 10,611,987 B2

ANTIFOAM MOLECULES CONTAINING A SILICA MOIETY AND COMPOSITIONS

FIELD OF THE INVENTION

The present application relates to cleaning and treatment compositions comprising a molecule that reduces foam and methods of making and using such molecule and compositions.

BACKGROUND OF THE INVENTION

Cleaning and/or treatment compositions may employ materials that produce suds. In certain cleaning and/or treatment compositions, the level of suds is higher than desired. One manner of reducing suds is to add an antifoamer to the cleaning and/or treatment composition. Unfortunately, the stability, and thus the performance of antifoams may, over time, be compromised by other formulation ingredients.

Applicants recognized that the source of the stability problem was certain moieties that are found on certain formulation ingredients. Such formulation ingredients include certain perfumes and solvents. While not being bound by theory, Applicants believe that the problems associated with such formulation ingredients arise as such formulation ingredients penetrate the antifoam and thus separate a key component of the antifoam from the remaining antifoam ingredients. Applicants recognized that such separation could be mitigated by covalently bonding the antifoam components together before incorporating them in the cleaning and treatment composition. While not being bound by theory, Applicants believe that such antifoam components react such that Si—O—Si groups are formed from the reaction of Si—OH and/or Si—OR groups on one antifoam component with another antifoam component's Si—OH and/or Si—OR groups wherein R is a methyl, ethyl, or propyl group and certain Si—O—Si groups already present before such reactions break and reform in a more preferred order thus yielding the superior antifoam. Such covalently bonded antifoam materials and compositions comprising same are disclosed herein.

SUMMARY OF THE INVENTION

The present application relates to cleaning and treatment compositions comprising a material that reduces foam and methods of making and using such material and compositions. Such compositions comprise benefit agents that typically impact the performance of antifoams, yet in the present compositions, antifoaming properties of antifoams are maintained.

DETAILED DESCRIPTION OF THE INVENTION

Definitions

As used herein, the term "cleaning and/or treatment composition" includes, unless otherwise indicated, unit dose, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations thereof.

As used herein, the articles "a" and "an" when used in a claim, are understood to mean one or more of what is claimed or described.

As used herein, the terms "include", "includes" and "including" are meant to be synonymous with the phrase "including but not limited to".

As used herein, the term "situs" includes paper products, fabrics, garments, hard surfaces, hair and skin.

As used to describe and/or recite the organomodified silicone element of the antifoams and cleaning and treatment compositions same herein, a 2-phenylpropylmethyl moiety is synonymous with: (methyl)(2-phenylpropyl); (2-Phenylpropyl)methyl; methyl(2-phenylpropyl); methyl((β-methylphenethyl); 2-phenylpropylmethyl; 2-phenylpropylmethyl; methyl 2-phenylpropyl; and Me 2-phenylpropyl. Thus, organomodified silicones can, by way of example, use nomenclature as follows:

(methyl)(2-phenylpropyl)siloxane
(methyl)(2-phenylpropyl) siloxane
(2-Phenylpropyl)methylsiloxane
(2-Phenylpropyl)methyl siloxane
methyl(2-phenylpropyl) siloxane
methyl(2-phenylpropyl) siloxane
methyl((β-methylphenethyl)siloxane
methyl((β-methylphenethyl) siloxane
2-phenylpropylmethylsiloxane
2-phenylpropylmethyl siloxane
2-phenylpropylMethylsiloxane
2-phenylpropylMethyl siloxane
methyl 2-phenylpropylsiloxane
methyl 2-phenylpropyl siloxane
Me 2-phenylpropylsiloxane As used herein, the term uninterrupted means the chain only comprises methylene groups.

As used herein, the term heteroatom takes it ordinary, customary meaning and thus includes N, O, S, P, Cl, Br, and I.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Molecules

A molecule having the formula

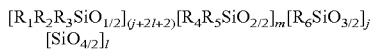

wherein:
a) j is an integer from 0 to 150, from 1 to 150, from 0 to 50, or from 0 to 20;
b) m is an integer from 0 to 1500, 0 to 1000, from 0 to 1000, or from 0 to 400;
c) l is an integer from 0 to 150, from 0 to 150, from 0 to 50, or from 0 to 20;
with the provisio j+m+l equals an integer greater than or equal to 1 and at least one of the moieties $R_1$ through $R_6$=X—Z;
d) each of $R_1$, $R_2$, $R_3$, $R_4$, $R_5$ and $R_6$ moiety is independently selected from the group consisting of H, OH, $C_1$-$C_{32}$ alkyl, $C_1$-$C_{32}$ substituted alkyl, $C_6$-$C_{32}$ aryl, $C_5$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy and X—Z, preferably each $R_{1-6}$ is independently selected from the group consisting of OH, $C_1$-$C_{12}$ alkyl, $C_1$-$C_{12}$ alkoxy, $C_1$-$C_{12}$ substituted alkoxy and X—Z;
e) each X is oxygen and
f) each Z is silica moiety, preferably said silica moiety is a particle or agglomerate, preferably said particle or agglomerate has a particle size (d50) from about 0.1 microns to about 250 microns, preferably from about 1 microns to about 100 microns, more preferably from about 4 microns to about 24 microns, most preferably from about 6 microns to about 13 microns.

is disclosed.

In one aspect of said molecule, at least one of $R_1$, $R_2$, $R_3$, $R_4$, $R_5$ and $R_6$ moieties comprise an aryl group, a phenyl group.

In one aspect of said molecule, said silica is selected from the group consisting of natural $SiO_2$ nanoparticles, synthetic $SiO_2$ nanoparticles and mixtures thereof; in one aspect, said synthetic $SiO_2$ nanoparticles comprise precipitated silica, fumed silica, and mixture thereof preferably said precipitated silica and fumed silica each have a Methanol Absorption Index of from 25 to 95, preferably from 40 to 80, more preferably from 60 to 70.

In one aspect of said molecule, said silica comprises a moiety selected from the group consisting of —OSi($R_7$)$_3$ wherein for said —OSi($R_7$)$_3$ each $R_7$ is independently $C_1$-$C_{22}$ alkyl group and/or $C_1$-$C_{22}$ substituted alkyl; —OH; $C_1$-$C_{22}$ alkoxy; $C_1$-$C_{22}$ substituted alkoxy; and mixtures thereof.

In one aspect of said molecule, the weight % of Z moieties in the molecule is from about 75% to about 99.99%, from about 85% to about 99.9%, from about 90% to about 99%, or from about 95% to about 98%.

Compositions Comprising Molecules

A composition comprising, based on total composition weight:
a) from about 2% to about 90%, from about 3% to about 60%, from about 5% to about 60%, or from about 5% to about 50% of a surfactant;
b) from about 0.1% to about 5%, from about 0.2% to about 3%, or from about 0.3% to about 2%, of an organic material having a molecular weight of from about 30 Da to about 350 Da, from about 50 Da to about 300 Da, or from about 100 Da to about 250 Da, said material comprising one or more of the following moieties:
(i) an aromatic moiety;
(ii) a cyclo aliphatic moiety; and
(iii) a non-cyclic aliphatic moiety comprising 1 to 10, or 2 to 7 methylene moieties, with the proviso that when said number of methylene moieties is greater than 1, said methylene moieties are uninterrupted, said non-cyclic aliphatic moiety being branched and/or comprising one or more double bonds,
with the provisos that said material does not comprise a siloxane moiety, and when said material comprises a non-cyclic aliphatic moiety but not an aromatic moiety and/or cyclo aliphatic moiety, said material has a logP of from about 2.0 to about 8.0, or from about 3.0 to about 6.0;
c) a carrier, in one aspect, the carrier comprises water and/or a water soluble solvent; and
d) from about 0.0001% to about 5%, from about 0.0005 to about 3%, from about 0.001% to about 1%, or from about 0.001% to about 0.5%, a molecule selected from the group consisting of the molecules disclosed in the Molecule section of this specification, and combinations of such molecules.

In one aspect of said composition, said composition comprises:
a) from about 0.001% to about 5%, from about 0.005% to about 3%, from about 0.01% to about 2%, or from about 0.01% to about 1% of an organomodified silicone comprising units of the following formula(I):

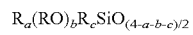 Formula (I)

wherein:
each R is independently selected from the group consisting of H, an aromatic hydrocarbon radical covalently attached to silicon via an aliphatic group, a monovalent, optionally substituted, aromatic hydrocarbon radical which is attached to the silicon atom via a carbon ring atom and a monovalent, SiC-bonded, optionally substituted, aliphatic hydrocarbon radical that optionally comprises a heteroatom;
the index a is 0, 1, 2 or 3;
the index b is 0, 1, 2 or 3;
the index c is 0, 1, 2 or 3;
with the proviso that:
for each of said Formula (I) units, the sum of indices a, b, and c is less than or equal to 3;
1% to 100% of said Formula (I) units, have an index c that is not 0;
for at least 50% of said Formula (I) units the sum of indices a, b, and c is 2; and
the sum of the mole percentage of R moieties in said organomodified silicone that are aromatic hydrocarbon radicals covalently attached to silicon via an aliphatic group, and/or a monovalent, optionally substituted, aromatic hydrocarbon radical which is attached to the silicon atom via a carbon ring atom is from about 1 mole percent to about 75 mole percent, 5 mole percent to 50 mole percent, or 5 mole percent to 40 mole percent, in one aspect, said organomodified silicone has a viscosity from 1,000 cSt to 10,000 cSt, from 2,000 cSt to 9,000 cSt, or from 5,000 cSt to 8,000 cSt; and
b) an optional solvent.

In one aspect of said composition, from about 1 mole percent to about 75 mole percent, 5 mole percent to 50 mole percent, or 5 mole percent to 40 mole percent of said organomodified silicone's R moieties are selected from the group consisting of 2-phenylpropyl moieties and/or phenyl moieties.

In one aspect of said composition, said composition comprises from about 0.001% to about 5%, from about 0.005% to about 3%, from about 0.01% to about 2%, or from about 0.01% to about 1% a silicone resin comprising units of the following formula(II):

$$R^3{}_d(R^4O)_e SiO_{(4-d-e)/2} \qquad \text{Formula (II)}$$

wherein:
a) each $R^3$ is independently selected from H, a monovalent, SiC-bonded, optionally substituted, aliphatic hydrocarbon radical that optionally comprises a heteroatom, or an aromatic hydrocarbon radical covalently attached to silicon via aliphatic groups;
b) each $R^4$ is independently selected from H, or a monovalent, optionally substituted aliphatic hydrocarbon radical, that optionally comprises a heteroatom;
c) the index d is 0, 1, 2 or 3; and
d) the index e is 0, 1, 2 or 3.

In one aspect of said composition, said surfactant is selected from the group consisting of anionic surfactants, cationic surfactants, nonionic surfactants, zwitterionic surfactants, ampholytic surfactants and mixtures thereof.

In one aspect, said perfume raw material is selected from the group consisting of benzyl acetate, beta naphthol methyl ether, ethyl vanillin, eugenol, hexyl cinnamic aldehyde, methyl benzoate, methyl beta-naphthyl ketone, methyl phenyl carbinyl acetate, 3-methyl-5-phenylpentanol, 2-methoxy-4-allylphenol, 4-phenyl-2-methyl-2-butanol, 1-phenyl-2-methyl-2-propanol, 3-ethoxy-4-hydroxybenzaldehyde, 4-hydroxy-3-methoxybenzaldehyde, 2-hexyl-3-phenyl-2-propenal, 4-methoxybenzaldehyde, methyl anthranilate, benzyl acetone, 1-(4-methoxyphenyl)ethanone, .alpha.-methyl-4-(1-methylethyl)-benzenepropanal, .beta.-methyl-3-(1-methylethyl)-benzenepropanal, 2-ethyl-.alpha., .alpha.-dimethyl-benzenepropanal, 1,3-benzodioxole-5-carboxaldehyde, 4-methoxy-.alpha.-methyl-benzenepropanal, 2H-1-benzopyran-2-one, phenyl ethyl acetate, (2,2-dimethoxyethyl)-benzene, octahydrocoumarin, 1-methoxy-4-methylbenzene, (E)-1-methoxy-4-(1-propenyl)benzene, dimethyl benzyl carbinyl acetate, methyl(1-methylethyl)benzene, camphene, 1-methoxy-4-methylbenzene, dimethyl benzyl carbinyl butyrate, ethyl methyl phenyl glycidate, phenyl ethyl iso butyrate, 1,1'-oxybisbenzene, phenoxy ethyl iso butyrate, [2-(3-methylbutoxy)ethyl]benzene, 1,2,3,4,4a,5,8,8a-octahydro-2,2,6,8-tetramethyl-1-naphthalenol, 2,5,5-trimethyl-1,2,3,4,4α,5,6,7-octahydro-2-naphthalenol, 2-methoxynaphthalene, 2-methyl-undecanal, allyl heptoate, 3a,4,5,6,7,7a-hexahydro-4,7-methano-1H-inden-6-ol propanoate, 3,7-dimethyl-trans-2,6-octadien-1-ol, 4-Methyl-3-decen-5-ol, 3,7-dimethyl-1,6-octadiene-3-ol, 2,6-dimethyl-7-octen-2-ol, 10-undecen-1-al, 4,7-methano-3a,4,5,6,7,7a-hexahydroinden-6-yl acetate, 2,6-dimethyl-5-heptenal, terpineol, undecenal, dodecanal, ethyl-2-methyl butyrate, hexyl acetate, 5-heptyldihydro-2(3H)-furanone, 1,1,2,3,3-pentamethyl-2,5,6,7-tetrahydroinden-4-one, ethyl 2 methyl pentanoate, 9-decen-1-ol, 3,7-dimethyl-6-octen-1-ol, 3,7,11-trimethyl-1,6,10-dodecatrien-3-ol, 8-,9 and 10-undecenal, trans-4-decenal, 4-(octahydro-4,7-methano-5H-inden-5-yliden)butanal, trans-2-dodecenal, 2-octanone, octanal, decanal, 6-butyltetrahydro-2H-pyran-2-one, undecenal, nonanal, 2,6,10-trimethyl-9-undecenal, 1-hydroxy-3-decanone, (Z)-3-hexen-1-ol acetate, (2-methylbutoxy) 2-propenyl acetic acid ester, [carbonic acid, 3-hexenyl methyl ester, (Z)-], cis-2-methyl-4-propyl-1,3-oxathiane, allyl caproate, methyl 2-octynoate, linalyl acetate, tetrahydro-6-pentyl-2H-pyran-2-one, 3,7-dimethyl-6-octen-1-yl acetate, 5-hexyldihydro-2(3H)-furanone, geranyl acetate, (Z)-3-hexenyl isobutyrate, tetrahydro-4-methyl-2-(2-methyl-1-propenyl)-2H-pyran, 1,3,5-undecatriene, 2-buten-1-one, 2,4,6-trimethyl-3-cyclohexene-1-carboxaldehyde, cyclohexanemethanol, (1-methyl-2-(1,2,2-trimethylbicyclo [3.1.0]-hex-3-ylmethyl)cyclopropyl)methanol, 2,4,6-trimethyl-3-cyclohexene-1-methanol, 4-penten-2-ol, 2-pentylcyclopentan-1-ol, 4-methyl-1-(1-methylethyl)-3-cyclohexen-1-ol, 5-methyl-2-(1-methylethyl)-cyclohexanol, (E)-4-(2,6,6-trimethyl-2-cyclohexen-1-yl)-3-buten-2-one, 1-methyl-4-(4-methylpentyl)-3-cyclohexene-1-carboxaldehyde, (1S)-6,6-dimethyl-2-methylene-bicyclo[3.1.1]heptanes, 2,6,6-trimethyl-bicyclo[3.1.1]hept-2-ene, 1-methyl-4-(1-methylethenyl)-cyclohexene, 2-(2-(4-methyl-3-cyclohexen-1-yl)propyl)cyclo-pentanone, cyclohexanepropanol, 2-(4-methyl-cyclohex-3-enyl)-propan-2-ol, 6-methoxy dicyclopentadiene carboxaldehyde, 1,7,7-trimethyl-(1R)-bicyclo[2.2.1]heptan-2-one, (1S -endo)-1,7,7-trimethyl-bicyclo[2.2.1]heptan-2-ol, 4-(2,6,6-trimethyl-1-cyclohexen-1-yl)-3-buten-2-one, 1,3,3-trimethyl-2-oxabicyclo[2.2.2] octane, 4-cycloocten-1-yl methyl ester and mixtures thereof.

In one aspect, said material is selected from the group consisting of benzyl acetate, beta naphthol methyl ether, ethyl vanillin, eugenol, hexyl cinnamic aldehyde, methyl benzoate, methyl beta-naphthyl ketone, methyl phenyl carbinyl acetate, methyl benzoate, methyl phenyl carbinyl acetate, 2-hexyl-3-phenyl-2-propenal, 4-methoxybenzaldehyde, .alpha.-methyl-4-(1-methylethyl)-benzenepropanal, .beta.-methyl-3-(1-methylethyl)-benzenepropanal, 1,1'-oxybisbenzene, 2-methoxynaphthalene, 2-methyl-undecanal, allyl heptoate, 3a,4,5,6,7,7a-hexahydro-4,7-Methano-1H-inden-6-ol propanoate, 3,7-dimethyl-trans-2,6-octadien-1-ol, 4-methyl-3-decen-5-ol, 3,7-dimethyl-1,6-octadiene-3-ol, 2,6-dimethyl-7-octen-2-ol, 10-undecen-1-al, 4,7-methano-3a,4,5,6,7,7a-hexahydroinden-6-yl acetate, 2,6-dimethyl-5-heptenal, terpineol, undecenal, dodecanal, ethyl-2-methyl butyrate, hexyl acetate, 5-heptyldihydro-2(3H)-furanone, 2-(2-(4-methyl-3-cyclohexen-1-yl)propyl)cyclo-pentanone, cyclohexanepropanol, 2-(4-methyl-cyclohex-3-enyl)-propan-2-ol, 6-methoxy dicyclopentadiene carboxaldehyde, 1,7,7-trimethyl-(1R)-bicyclo[2.2.1]heptan-2-one, (1S-endo)-1,7,7-trimethyl-bicyclo[2.2.1]heptan-2-ol, 4-(2,6,6-trimethyl-1-cyclohexen-1-yl)-3-buten-2-one, 1,3,3-trimethyl-2-oxabicyclo[2.2.2]octane, 4-cycloocten-1-yl methyl ester and mixtures thereof. In one aspect, said material is selected from the group consisting of benzyl acetate, beta naphthol methyl ether, ethyl vanillin, eugenol, hexyl cinnamic aldehyde, methyl benzoate, methyl beta-naphthyl ketone, methyl phenyl carbinyl acetate,1-(2,6,6-trimethyl-3-cyclohexen-1-yl)-2-buten-1-one, 1-(5,5-dimethyl-1-cyclohexenyl)pent-4-en-1-one, dimethyl-3-cyclohexene-1-carboxaldehyde, α-Isomethyl ionone, ethyl trimethylcyclopentene butenol, 2-(1,1-dimethylethyl)-cyclohexanol acetate, 1,7,7-trimethyl-, acetate, exo-bicyclo [2.2.1]heptan-2-ol, 2-propenyl ester cyclohexanepropanoic acid, 2-methyl-undecanal, allyl heptoate, 3a,4,5,6,7,7a-hexahydro-4,7-Methano-1H-inden-6-ol propanoate and mixtures thereof.

In one aspect of said composition, said organic compound contains an aromatic moiety. In one aspect of said composition, said composition comprises an adjunct ingredient selected from the group consisting of color care polymers, deposition aid polymers, surfactant boosting polymers, pH adjusters, product color stabilizers, preservatives, solvents, builders, chelating agents, dye transfer inhibiting agents, dispersants, enzymes, and enzyme stabilizers, catalytic materials, bleach, bleach activators, polymeric dispersing agents, clay soil removal/anti-redeposition agents, brighteners, suds suppressors, dyes, UV absorbers, perfume in addition to said organic material, perfume delivery systems, structure elasticizing agents, thickeners/structurants, fabric softeners, hydrotropes, oligoamines, processing aids, hueing agents, and/or pigments.

In one aspect of said composition:

a) said fabric softener active is selected from the group consisting of polyglycerol esters, oily sugar derivatives, wax emulsions, fatty acids, N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate and mixtures thereof;

b) said deposition aid polymer comprises a cationic polymer having a cationic charge of from about 0.005 meq/g to about 23 meq/g, from about 0.01 meq/g to about 12 meq/g, or from about 0.1 meq/g to about 7 meq/g at the pH of said composition;

c) said perfume delivery system comprises components selected from the group consisting of a perfume microcapsule, or a moisture-activated perfume microcapsule, wherein the microcapsule comprises a shell comprising a polyacrylate and/or a polymer crosslinked with an aldehyde, in one aspect, said shell comprises a polymer selected from the group consisting of a polyacrylate, polyurea, polyurethane, polyamine, urea crosslinked with an aldehyde, or melamine crosslinked with an aldehyde, in another aspect, said polymer is selected from the group consisting of melamine-formaldehyde, urea-formaldehyde, phenol-formaldehyde, or other condensation polymers with formaldehyde, a perfume carrier and an encapsulated perfume composition, wherein said perfume carrier may be selected from the group consisting of cyclodextrins, starch microcapsules, porous carrier microcapsules, and mixtures thereof; and wherein said encapsulated perfume composition may comprise low volatile perfume ingredients, high volatile perfume ingredients, and mixtures thereof;

d) said enzyme is selected from the group consisting of protease, amylase, lipase, mannanase, cellulase, xyloglucanase, pectate lyase, and mixtures thereof;

e) said structurant is selected from the group of hydrogenated castor oil; derivatives of hydrogenated castor oil; microfibrillar cellulose; hydroxyfunctional crystalline materials, long-chain fatty alcohols, 12-hydroxystearic acid; clays; and mixtures thereof;

f) said polymeric dispersing agent is selected from the group consisting of polycarboxylates, soil release polymers, carboxymethylcelluloses, poly(vinyl-pyrrolidone), poly (ethylene glycol), poly(vinyl alcohol), poly (vinylpyridine-N-oxide), poly(vinylimidazole), zwitterionic ethoxylated quaternized sulfated hexamethylene diamine, alkoxylated polyalkylenimine, ethoxylated polyamine, polyethylene glycol-polyvinylacetate;

g) said hueing agent is selected from the group consisting of from the group consisting of small molecule dyes, polymeric dyes, dye clay conjugates and pigments;

h) said oligoamine is selected from the group consisting of polyetheramines; and i) mixtures thereof.

In one aspect, said composition comprises an anionic surfactant. In one aspect, said anionic surfactant is selected from the group consisting of a $C_9$-$C_{18}$ alkyl benzene sulfonate surfactant; a $C_{10}$-$C_{20}$ alkyl sulfate surfactant; a $C_{10}$-$C_{18}$ alkyl alkoxy sulfate surfactant, said $C_{10}$-$C_{18}$ alkyl alkoxy sulfate surfactant having an average degree of alkoxylation of from 1 to 30 and the alkoxy comprises a $C_1$-$C_4$ chain, and mixtures thereof.

In one aspect, said composition comprises a fabric softener active. In one aspect, said fabric softener active is selected from the group consisting of N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate, bis-(2-hydroxypropyl)-dimethyl-ammonium methylsulfate fatty acid ester and mixtures thereof. In one aspect, said fabric softener active comprises one or more ester quats. In one aspect, said ester quats are a reaction product of Methyl-diethanolamine with one or more fatty acids, in a molar ratio ranging from 1:1.5 to 1:2, fully or partially quaternized with methylchloride or dimethylsulphate; the reaction product of Tri-ethanolamine with one or more fatty acids, mixed in a molar ratio ranging from 1:1.5 to 1:2.1, fully or partially quaternized with dimethylsulphate; and/or is the reaction product of Methyl-diethanolamine with one or more fatty acids, fully or partially quaternized with dimethylsulphate. In one aspect, said fatty acids comprise 8-24 carbon atoms and have an iodine value of 0-100, 5-80, 15-70, or 18-56.

Additional Disclosure

Molecule

A molecule having the formula

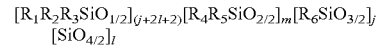

wherein:

a) j is an integer from 0 to 150, preferably from 1 to 150, more preferably from 0 to 50, most preferably from 0 to 20;

b) m is an integer from 0 to 1500, preferably 0 to 1000, more preferably from 0 to 1000, most preferably from 0 to 400;

c) l is an integer from 0 to 150, preferably from 0 to 150, more preferably from 0 to 50, most preferably from 0 to 20;

with the provisio j+m+l equals an integer greater than or equal to 1 and at least one of the moieties $R_1$ through $R_6$ =X—Z;

d) each of $R_1$, $R_2$, $R_3$, $R_4$, $R_5$ and $R_6$ moiety is independently selected from the group consisting of H, OH, $C_1$-$C_{32}$ alkyl, $C_1$-$C_{32}$ substituted alkyl, $C_6$-$C_{32}$ aryl, $C_5$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy and X—Z, preferably each $R_{1-6}$ is independently selected from the group consisting of OH, $C_1$-$C_{12}$ alkyl, $C_1$-$C_{12}$ alkoxy, $C_1$-$C_{12}$ substituted alkoxy and X—Z;

e) each X is oxygen and f) each Z is silica moiety, preferably said silica moiety is a particle or agglomerate, preferably said particle or agglomerate has a particle size (d50) from about 0.1 microns to about 250 microns, preferably from about 1 microns to about 100 microns, more preferably from about 4 microns to about 24 microns, most preferably from about 6 microns to about 13 microns.

is disclosed.

Preferably at least one of $R_1$, $R_2$, $R_3$, $R_4$, $R_5$ and $R_6$ moieties comprise an aryl group, preferably a phenyl group.

Preferably said silica is selected from the group consisting of natural $SiO_2$ nanoparticles, synthetic $SiO_2$ nanoparticles and mixtures thereof; preferably said synthetic $SiO_2$ nanoparticles comprise precipitated silica, fumed silica, and mixture thereof, preferably said precipitated silica and fumed silica each have a Methanol Absorption Index of from 25 to 95, preferably from 40 to 80, more preferably from 60 to 70.

Preferably said silica comprises a moiety selected from the group consisting of —$OSi(R_7)_3$ wherein for said —$OSi(R_7)_3$ each $R_7$ is independently $C_1$-$C_{22}$ alkyl group and/or $C_1$-$C_{22}$ substituted alkyl; —OH; $C_1$-$C_{22}$ alkoxy; $C_1$-$C_{22}$ substituted alkoxy; and mixtures thereof.

Preferably the weight % of Z moieties in the molecule is from 75% to 99.99%, preferably from 85% to 99.9%, more preferably from 90% to 99%, most preferably from 95% to 98%.

Compositions Comprising Molecules

A composition comprising, based on total composition weight:
a) from 2% to 90%, preferably from 3% to 60%, more preferably from 5% to 60%, most preferably from 5% to 50% of a surfactant;
b) from 0.1% to 5%, preferably from 0.2% to 3%, more preferably from 0.3% to 2%, of an organic material having a molecular weight of from 30 Da to 350 Da, preferably from 50 Da to 300 Da, more preferably from 100 Da to 250 Da, said material comprising one or more of the following moieties:
 (i) an aromatic moiety;
 (ii) a cyclo aliphatic moiety; and
 (iii) a non-cyclic aliphatic moiety comprising 1 to 10, preferably 2 to 7 methylene moieties, with the proviso that when said number of methylene moieties is greater than 1, said methylene moieties are uninterrupted, said non-cyclic aliphatic moiety being branched and/or comprising one or more double bonds,
with the provisos that said material does not comprise a siloxane moiety, and when said material comprises a non-cyclic aliphatic moiety but not an aromatic moiety and/or cyclo aliphatic moiety, said material has a logP of from 2.0 to 8.0, preferably from 3.0 to 6.0;
c) a carrier, preferably the carrier comprises water and/or a water soluble solvent; and
d) from 0.0001% to 5%, preferably from 0.0005 to 3%, more preferably from 0.001% to 1%, most preferably from 0.001% to 0.5%, a molecule selected from the group consisting of the molecules disclosed in the Molecule section of this specification, and combinations of such molecules is disclosed.

Preferably, said composition comprises:
c) from 0.001% to 5%, preferably from 0.005% to 3%, more preferably from 0.01% to 2%, most preferably from 0.01% to 1% an organomodified silicone comprising units of the following formula(I):

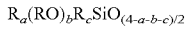  Formula (I)

wherein:
each R is independently selected from the group consisting of H, an aromatic hydrocarbon radical covalently attached to silicon via an aliphatic group, a monovalent, optionally substituted, aromatic hydrocarbon radical which is attached to the silicon atom via a carbon ring atom and a monovalent, SiC-bonded, optionally substituted, aliphatic hydrocarbon radical that optionally comprises a heteroatom;
the index a is 0, 1, 2 or 3;
the index b is 0, 1, 2 or 3;
the index c is 0, 1, 2 or 3;
with the proviso that:
 for each of said Formula (I) units, the sum of indices a, b, and c is less than or equal to 3;
 1% to 100% of said Formula (I) units, have an index c that is not 0;
 for at least 50% of said Formula (I) units the sum of indices a, b, and c is 2; and
 the sum of the mole percentage of R moieties in said organomodified silicone that are aromatic hydrocarbon radicals covalently attached to silicon via an aliphatic group, and/or a monovalent, optionally substituted, aromatic hydrocarbon radical which is attached to the silicon atom via a carbon ring atom is from 1 mole percent to 75 mole percent, preferably 5 mole percent to 50 mole percent, more preferably 5 mole percent to 40 mole percent, preferably said organomodified silicone has a viscosity from 1,000cSt to 10,000cSt, more preferably from 2,000cSt to 9,000cSt, most preferably from 5,000cSt to 8,000cSt; and
d) an optional solvent.

Preferably from 1 mole percent to 75 mole percent, preferably 5 mole percent to 50 mole percent, more preferably 5 mole percent to 40 mole percent of said organomodified silicone's R moieties are selected from the group consisting of 2-phenylpropyl moieties and/or phenyl moieties.

Preferably said composition comprises from 0.001% to 5%, preferably from 0.005% to 3%, more preferably from 0.01% to 2%, most preferably from 0.01% to 1% a silicone resin comprising units of the following formula(II):

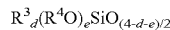  Formula (II)

wherein:
e) each $R^3$ is independently selected from H, a monovalent, SiC-bonded, optionally substituted, aliphatic hydrocarbon radical that optionally comprises a heteroatom, or an aromatic hydrocarbon radical covalently attached to silicon via aliphatic groups;
f) each $R^4$ is independently selected from H, or a monovalent, optionally substituted aliphatic hydrocarbon radical, that optionally comprises a heteroatom;
g) the index d is 0, 1, 2 or 3; and
h) the index e is 0, 1, 2 or 3.

Preferably, said surfactant is selected from the group consisting of anionic surfactants, cationic surfactants, nonionic surfactants, zwitterionic surfactants, ampholytic surfactants and mixtures thereof.

Preferably, said organic material comprises a perfume raw material, preferably said perfume raw material is selected from the group consisting of benzyl acetate, beta naphthol methyl ether, ethyl vanillin, eugenol, hexyl cinnamic aldehyde, methyl benzoate, methyl beta-naphthyl ketone, methyl phenyl carbinyl acetate, 3-methyl-5-phenylpentanol, 2-methoxy-4-allylphenol, 4-phenyl-2-methyl-2-butanol, 1-phenyl-2-methyl-2-propanol, 3-ethoxy-4-hydroxybenzaldehyde, 4-hydroxy-3-methoxybenzaldehyde, 2-hexyl-3-phenyl-2-propenal, 4-methoxybenzaldehyde, methyl anthranilate, benzyl acetone, 1-(4-methoxyphenyl)ethanone, .alpha.-methyl-4-(1-methylethyl)-benzenepropanal, .beta.-methyl-3-(1-methylethyl)-benzenepropanal, 2-ethyl-.alpha.,.alpha.-dimethyl-benzenepropanal, 1,3-benzodioxole-5-carboxaldehyde, 4-methoxy-.alpha.-methyl-benzenepropanal, 2H-1-benzopyran-2-one, phenyl ethyl acetate, (2,2-dimethoxyethyl)-benzene, octahydrocoumarin, 1-methoxy-4-methylbenzene, (E)-1-methoxy-4-(1-propenyl)benzene, dimethyl benzyl carbinyl acetate, methyl(1-methylethyl)benzene, camphene, 1-methoxy-4-methylbenzene, dimethyl benzyl carbinyl butyrate, ethyl methyl phenyl glycidate, phenyl ethyl iso butyrate, 1,1'-oxybisbenzene, phenoxy ethyl iso butyrate, [2-(3-methylbutoxy)ethyl]benzene, 1,2,3,4,4a,5,8,8a-octahydro-2,2,6,8-tetramethyl-1-naphthalenol, 2,5,5-trimethyl-1,2,3,4,4a,5,6,7-octahydro-2-naphthalenol, 2-methoxynaphthalene, 2-methyl-undecanal, allyl heptoate, 3a,4,5,6,7,7a-hexahydro-4,7-methano-1H-inden-6-ol propanoate, 3,7-dimethyl-trans-2,6-octadien-1-ol, 4-Methyl-3-decen-5-ol, 3,7-dimethyl-1,6-octadiene-3-ol, 2,6-dimethyl-7-octen-2-ol, 10-undecen-1-al, 4,7-methano-3a,4,5,6,7,7a-hexahydroinden-6-yl acetate, 2,6-dimethyl-5-heptenal, terpineol, undecenal, dodecanal, ethyl-2-methyl butyrate, hexyl acetate, 5-heptyldihydro-2(3H)-furanone, 1,1,2,3,3-pentamethyl-2,5,6,7-tetrahydroinden-4-one, ethyl 2 methyl pentanoate, 9-decen-1-ol, 3,7-dimethyl-6-octen-1-ol, 3,7,11-trimethyl-1,6,10-dodecatrien-3-ol, 8-,9 and 10-undecenal, trans-4-decenal, 4-(octahydro-4,7-methano-5H-inden-5-yliden)butanal, trans-2-dodecenal, 2-octanone, octanal, decanal, 6-butyltetrahydro-2H-pyran-2-one, undecenal, nonanal, 2,6,10-trimethyl-9-undecenal, 1-hydroxy-3-decanone, (Z)-3-hexen-1-ol acetate, (2-methylbutoxy) 2-propenyl acetic acid ester, [carbonic acid, 3-hexenyl methyl ester, (Z)-], cis-2-methyl-4-propyl-1,3-oxathiane, allyl caproate, methyl 2-octynoate, linalyl acetate, tetrahydro-6-pentyl-2H-pyran-2-one, 3,7-dimethyl-6-octen-1-yl acetate, 5-hexyldihydro-2(3H)-furanone, geranyl acetate, (Z)-3-hexenyl isobutyrate, tetrahydro-4-methyl-2-(2-methyl-1-propenyl)-2H-pyran, 1,3,5-undecatriene, 2-buten-1-one, 2,4,6-trimethyl-3-cyclohexene-1-carboxaldehyde, cyclohexanemethanol, (1-methyl-2-(1,2,2-trimethylbicyclo[3.1.0]-hex-3-ylmethyl)cyclopropyl)methanol, 2,4,6-trimethyl-3-cyclohexene-1-methanol, 4-penten-2-ol, 2-pentylcyclopentan-1-ol, 4-methyl-1-(1-methylethyl)-3-cyclohexen-1-ol, 5-methyl-2-(1-methylethyl)-cyclohexanol, (E)-4-(2,6,6-trimethyl-2-cyclohexen-1-yl)-3-buten-2-one, 1-methyl-4-(4-methylpentyl)-3-cyclohexene-1-carboxaldehyde, (1S)-6,6-dimethyl-2-methylene-bicyclo[3.1.1]heptanes, 2,6,6-trimethyl-bicyclo[3.1.1]hept-2-ene, 1-methyl-4-(1-methylethenyl)-cyclohexene, 2-(2-(4-methyl-3-cyclohexen-1-yl)propyl)cyclo-pentanone, cyclohexanepropanol, 2-(4-methyl-cyclohex-3-enyl)-propan-2-ol, 6-methoxy dicyclopentadiene carboxaldehyde, 1,7,7-trimethyl-(1R)-bicyclo[2.2.1]heptan-2-one, (1S-endo)-1,7,7-trimethyl-bicyclo[2.2.1]heptan-2-ol, 4-(2,6,6-trimethyl-1-cyclohexen-1-yl)-3-buten-2-one, 1,3,3-trimethyl-2-oxabicyclo[2.2.2]octane, 4-cycloocten-1-yl methyl ester and mixtures thereof, more preferably said material is selected from the group consisting of benzyl acetate, beta naphthol methyl ether, ethyl vanillin, eugenol, hexyl cinnamic aldehyde, methyl benzoate, methyl beta-naphthyl ketone, methyl phenyl carbinyl acetate, 2-hexyl-3-phenyl-2-propenal, 4-methoxybenzaldehyde, .alpha.-methyl-4-(1-methylethyl)-benzenepropanal, .beta.-methyl-3-(1-methylethyl)-benzenepropanal, 1,1'-oxybisbenzene, 2-methoxynaphthalene, 2-methyl-undecanal, allyl heptoate, 3a,4,5,6,7,7a-hexahydro-4,7-Methano-1H-inden-6-ol propanoate, 3,7-dimethyl-trans-2,6-octadien-1-ol, 4-methyl-3-decen-5-ol, 3,7-dimethyl-1,6-octadiene-3-ol, 2,6-dimethyl-7-octen-2-ol, 10-undecen-1-al, 4,7-methano-3a,4,5,6,7,7a-hexahydroinden-6-yl acetate, 2,6-dimethyl-5-heptenal, terpineol, undecenal, dodecanal, ethyl-2-methyl butyrate, hexyl acetate, 5-heptyldihydro-2(3H)-furanone, 2-(2-(4-methyl-3-cyclohexen-1-yl)propyl)cyclo-pentanone, cyclohexanepropanol, 2-(4-methyl-cyclohex-3-enyl)-propan-2-ol, 6-methoxy dicyclopentadiene carboxaldehyde, 1,7,7-trimethyl-(1R)-bicyclo[2.2.1]heptan-2-one, (1S-endo)-1,7,7-trimethyl-bicyclo[2.2.1]heptan-2-ol, 4-(2,6,6-trimethyl-1-cyclohexen-1-yl)-3-buten-2-one, 1,3,3-trimethyl-2-oxabicyclo[2.2.2]octane, 4-cycloocten-1-yl methyl ester and mixtures thereof, most preferably said material is selected from the group consisting of benzyl acetate, beta naphthol methyl ether, ethyl vanillin, eugenol, hexyl cinnamic aldehyde, methyl benzoate, methyl beta-naphthyl ketone, methyl phenyl carbinyl acetate,1-(2,6,6-trimethyl-3-cyclohexen-1-yl)-2-buten-1-one, 1-(5,5-dimethyl-1-cyclohexenyl)pent-4-en-1-one, dimethyl-3-cyclohexene-1-carboxaldehyde, α-Isomethyl ionone, ethyl trimethylcyclopentene butenol, 2-(1,1-dimethylethyl)-cyclohexanol acetate, 1,7,7-trimethyl-, acetate, exo-bicyclo[2.2.1]heptan-2-ol, 2-propenyl ester cyclohexanepropanoic acid, 2-methyl-undecanal, allyl heptoate, 3a,4,5,6,7,7a-hexahydro-4,7-Methano-1H-inden-6-ol propanoate and mixtures thereof.

Preferably the organic compound comprises an aromatic moiety.

Preferably, said silicone resin comprises units of formula (II) below:

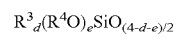   Formula (II)

wherein:
a) each $R^3$ is independently selected from H, a monovalent, SiC-bonded, optionally substituted, aliphatic hydrocarbon radical that optionally comprises a heteroatom, or an aromatic hydrocarbon radical covalently attached to silicon via aliphatic groups;
b) each $R^4$ is independently selected from H, or a monovalent, optionally substituted aliphatic hydrocarbon radical, that optionally comprises a heteroatom;
c) the index d is 0, 1, 2 or 3; and
d) the index e is 0, 1, 2 or 3.

Preferably, said composition comprises an adjunct ingredient selected from the group consisting of color care polymers, deposition aids, surfactant boosting polymers, pH adjusters, product color stabilizers, preservatives, solvents, builders, chelating agents, dye transfer inhibiting agents, dispersants, enzymes, and enzyme stabilizers, catalytic materials, bleach, bleach activators, polymeric dispersing agents, clay soil removal/anti-redeposition agents, brighteners, suds suppressors, dyes, UV absorbers, perfume in addition to the organic material, perfume delivery systems, structure elasticizing agents, thickeners/structurants, fabric softeners, hydrotropes, oligoamines, processing aids, hueing agents, and/or pigments.

Preferably
a) said fabric softener active is selected from the group consisting of polyglycerol esters, oily sugar derivatives, wax emulsions, fatty acids, N,N-bis(stearoyloxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate and mixtures thereof;
b) said deposition aid polymer comprises a cationic polymer having a cationic charge of from 0.005 meq/g to 23 meq/g, preferably of from 0.01 meq/g to 12 meq/g, most preferably of from 0.1 meq/g to 7 meq/g at the pH of said composition;
c) said perfume delivery system comprises components selected from the group consisting of a perfume microcapsule, or a moisture-activated perfume microcapsule, wherein the microcapsule comprises a shell comprising a polyacrylate and/or a polymer crosslinked with an aldehyde, preferably said shell comprises a polymer selected from the group consisting of a polyacrylate, polyurea, polyurethane, polyamine, urea crosslinked with an aldehyde, or melamine crosslinked with an aldehyde, more preferably said polymer is selected from the group consisting of melamine-formaldehyde, urea-formaldehyde, phenol-formaldehyde, or other condensation polymers with formaldehyde, a perfume carrier and an encapsulated perfume composition, wherein said perfume carrier may be selected from the group consisting of cyclodextrins, starch microcapsules, porous carrier microcapsules, and mixtures thereof; and wherein said encapsulated perfume composition may comprise low volatile perfume ingredients, high volatile perfume ingredients, and mixtures thereof;
d) said enzyme is selected from the group consisting of protease, amylase, lipase, mannanase, cellulase, xyloglucanase, pectate lyase, and mixtures thereof;
e) said structurant is selected from the group of hydrogenated castor oil; derivatives of hydrogenated castor oil; microfibrillar cellulose; hydroxyfunctional crystalline materials, long-chain fatty alcohols, 12-hydroxystearic acid; clays; and mixtures thereof;
f) said polymeric dispersing agent is selected from the group consisting of polycarboxylates, soil release polymers, carboxymethylcelluloses, poly(vinyl-pyrrolidone), poly (ethylene glycol), poly(vinyl alcohol), poly (vinylpyridine-N-oxide), poly(vinylimidazole), zwitterionic ethoxylated quaternized sulfated hexamethylene diamine, alkoxylated polyalkylenimine, ethoxylated polyamine, polyethylene glycol-polyvinylacetate;
g) said hueing agent is selected from the group consisting of from the group consisting of small molecule dyes, polymeric dyes, dye clay conjugates and pigments;
h) said oligoamine is selected from the group consisting of polyetheramines; and
i) mixtures thereof.

Preferably said composition comprises an anionic surfactant, preferably said anionic surfactant is selected from the group consisting of a $C_9$-$C_{18}$ alkyl benzene sulfonate surfactant; a $C_{10}$-$C_{20}$ alkyl sulfate surfactant; a $C_{10}$-$C_{18}$ alkyl alkoxy sulfate surfactant, said $C_{10}$-$C_{18}$ alkyl alkoxy sulfate surfactant having an average degree of alkoxylation of from 1 to 30 and the alkoxy comprises a $C_1$-$C_4$ chain, and mixtures thereof. When said composition comprises an anionic surfactant, said composition can comprise another surfactant but in most cases will not comprise a cationic surfactant or a cationic fabric softener active.

Preferably, said composition comprises a fabric softener active, preferably said fabric softener active is selected from the group consisting of N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate, bis-(2-hydroxypropyl)-dimethylammonium methylsulfate fatty acid ester and mixtures thereof.

Preferably, said composition comprises a fabric softener active that comprises one or more ester quats, preferably said ester quats are reaction products of Methyl-diethanolamine with one or more fatty acids, in a molar ratio ranging from 1:1.5 to 1:2, fully or partially quaternized with methylchloride or dimethylsulphate; the reaction product of Tri-ethanolamine with one or more fatty acids, mixed in a molar ratio ranging from 1:1.5 to 1:2.1, fully or partially quaternized with dimethylsulphate; and/or is the reaction product of Methyl-diethanolamine with fatty acids, fully or partially quaternized with dimethylsulphate; preferably, said one or more fatty acid contains 8-24 carbon atoms and has an iodine value of 0-100, preferably 5-80, more preferably 15-70, most preferably 18-56.

Process of Making

The molecules and compositions disclosed and/or claimed herein can be made by in accordance with the teachings of the present specification, including the examples.

The consumer products disclosed and/or claimed herein can be made by in accordance with the teachings of the present specification, including the examples. In one aspect, such compositions can be made by combining one or more of molecule disclosed and/or claimed herein with an adjunct ingredient Method of Use In one aspect, a method of treating and/or cleaning a situs, said method comprising
 a) optionally washing and/or rinsing said situs;
 b) contacting said situs with an antifoam composition and/or a cleaning or treatment composition disclosed or claimed in the present specification;
 c) optionally washing and/or rinsing said situs; and
 d) optionally drying said situs via passive or active drying
is disclosed.

Adjunct Materials

While not essential for each consumer product embodiment of the present invention, the non-limiting list of adjuncts illustrated hereinafter are suitable for use in the instant cleaning or treatment compositions and may be desirably incorporated in certain embodiments of the invention, for example to assist or enhance performance, for treatment of the substrate to be cleaned, or to modify the aesthetics of the composition as is the case with perfumes, colorants, dyes or the like. The precise nature of these additional components, and levels of incorporation thereof, will depend on the physical form of the composition and the nature of the operation for which it is to be used. Suitable adjunct materials include, but are not limited to surfactants, color care polymers, deposition aids, surfactant boosting polymers, pH adjusters, product color stabilizers, preservatives, solvents, builders, chelating agents, dye transfer inhibiting agents, dispersants, enzymes, and enzyme stabilizers, catalytic materials, bleach, bleach activators, polymeric dispersing agents, clay soil removal/anti-redeposition agents, brighteners, suds suppressors, dyes, UV absorbers, perfume in addition to the organic material, perfume delivery systems, structure elasticizing agents, thickeners/structurants, fabric softeners, carriers, hydrotropes, oligoamines, processing aids, hueing agents, and/or pigments.

As stated, the adjunct ingredients are not essential for each consumer product embodiment of the present invention. Thus, certain embodiments of Applicants' compositions do not contain one or more of the following adjuncts materials: surfactants, color care polymers, deposition aids, surfactant boosting polymers, pH adjusters, product color stabilizers, preservatives, solvents, builders, chelating agents, dye transfer inhibiting agents, dispersants, enzymes, and enzyme stabilizers, catalytic materials, bleach, bleach activators, polymeric dispersing agents, clay soil removal/anti-redeposition agents, brighteners, suds suppressors, dyes, UV absorbers, perfume and perfume delivery systems, structure elasticizing agents, thickeners/structurants, fabric softeners, carriers, hydrotropes, oligoamines, processing aids, hueing agents, and/or pigments. However, when one or more adjuncts is present, such one or more adjuncts may be present as detailed below.

Surfactants

In some examples, the additional surfactant comprises one or more anionic surfactants. In some examples, the additional surfactant may consist essentially of, or even consist of one or more anionic surfactants.

Specific, non-limiting examples of suitable anionic surfactants include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates.

Alkoxylated alkyl sulfate materials comprise ethoxylated alkyl sulfate surfactants, also known as alkyl ether sulfates or alkyl polyethoxylate sulfates. Examples of ethoxylated alkyl sulfates include water-soluble salts, particularly the alkali metal, ammonium and alkylolammonium salts, of organic sulfuric reaction products having in their molecular structure an alkyl group containing from about 8 to about 30 carbon atoms and a sulfonic acid and its salts. (Included in the term "alkyl" is the alkyl portion of acyl groups. In some examples, the alkyl group contains from about 15 carbon atoms to about 30 carbon atoms. In other examples, the alkyl ether sulfate surfactant may be a mixture of alkyl ether sulfates, said mixture having an average (arithmetic mean) carbon chain length within the range of about 12 to 30 carbon atoms, and in some examples an average carbon chain length of about 12-15 carbon atoms, and an average (arithmetic mean) degree of ethoxylation of from about 1 mol to 4 mols of ethylene oxide, and in some examples an average (arithmetic mean) degree of ethoxylation of about 1.8 mols to about 4 mols of ethylene oxide. In further examples, the alkyl ether sulfate surfactant may have a carbon chain length between about 10 carbon atoms to about 18 carbon atoms, and a degree of ethoxylation of from about 1 to about 6 mols of ethylene oxide. In yet further examples, the alkyl ether sulfate surfactant may contain a peaked ethoxylate distribution, Non-ethoxylated alkyl sulfates may also be added to the disclosed cleaning compositions and used as an anionic surfactant component. Examples of non-alkoxylated, e.g., non-ethoxylated, alkyl sulfate surfactants include those produced by the sulfation of higher $C_8$-$C_{20}$ fatty alcohols. In some examples, primary alkyl sulfate surfactants have the general formula: $ROSO_3^-M^+$, wherein R is typically a linear $C_8$-$C_{20}$ hydrocarbyl group, which may be straight chain or branched chain, and M is a water-solubilizing cation. In some examples, R is a $C_{10}$-$C_{15}$ alkyl, and M is an alkali metal. In other examples, R is a $C_{12}$-$C_{14}$ alkyl and M is sodium.

Other useful anionic surfactants can include the alkali metal salts of alkyl benzene sulfonates, in which the alkyl group contains from about 9 to about 15 carbon atoms, in straight chain (linear) or branched chain configuration, e.g. those of the type described in U.S. Pat. Nos. 2,220,099 and 2,477,383. In some examples, the alkyl group is linear. Such linear alkylbenzene sulfonates are known as "LAS." In other examples, the linear alkylbenzene sulfonate may have an average number of carbon atoms in the alkyl group of from about 11 to 14. In a specific example, the linear straight chain alkyl benzene sulfonates may have an average number of carbon atoms in the alkyl group of about 11.8 carbon atoms, which may be abbreviated as C11.8 LAS.

Suitable alkyl benzene sulphonate (LAS) may be obtained, by sulphonating commercially available linear alkyl benzene (LAB); suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic detersive surfactant is alkyl benzene sulphonate that is obtained by DETAL catalyzed process, although other synthesis routes, such as HF, may also be suitable. In one aspect a magnesium salt of LAS is used.

The detersive surfactant may be a mid-chain branched detersive surfactant, in one aspect, a mid-chain branched anionic detersive surfactant, in one aspect, a mid-chain branched alkyl sulphate and/or a mid-chain branched alkyl benzene sulphonate, for example, a mid-chain branched alkyl sulphate. In one aspect, the mid-chain branches are $C_{1-4}$ alkyl groups, typically methyl and/or ethyl groups.

Other anionic surfactants useful herein are the water-soluble salts of: paraffin sulfonates and secondary alkane sulfonates containing from about 8 to about 24 (and in some examples about 12 to 18) carbon atoms; alkyl glyceryl ether sulfonates, especially those ethers of $C_{8-18}$ alcohols (e.g., those derived from tallow and coconut oil). Mixtures of the alkylbenzene sulfonates with the above-described paraffin sulfonates, secondary alkane sulfonates and alkyl glyceryl ether sulfonates are also useful. Further suitable anionic surfactants include methyl ester sulfonates and alkyl ether carboxylates.

The anionic surfactants may exist in an acid form, and the acid form may be neutralized to form a surfactant salt. Typical agents for neutralization include metal counterion bases, such as hydroxides, e.g., NaOH or KOH. Further suitable agents for neutralizing anionic surfactants in their acid forms include ammonia, amines, or alkanolamines. Non-limiting examples of alkanolamines include monoethanolamine, diethanolamine, triethanolamine, and other linear or branched alkanolamines known in the art; suitable alkanolamines include 2-amino-1-propanol, 1-aminopropanol, monoisopropanolamine, or 1-amino-3-propanol. Amine neutralization may be done to a full or partial extent, e.g., part of the anionic surfactant mix may be neutralized with sodium or potassium and part of the anionic surfactant mix may be neutralized with amines or alkanolamines.

Nonionic surfactants

In some aspects, the additional surfactant comprises one or more nonionic surfactants. In certain aspects, the detergent composition comprises from about 0.1% to about 40%, by weight of the composition, of an additional surfactant selected from one or more nonionic surfactants. In certain aspects, the detergent composition comprises from about 0.1% to about 15%, by weight of the composition, of an additional surfactant selected from one or more nonionic surfactants. In further aspects, the detergent composition comprises from about 0.3% to about 10%, by weight of the composition, of an additional surfactant selected from one or more nonionic surfactants.

Suitable nonionic surfactants useful herein can comprise any conventional nonionic surfactant. These can include, for e.g., alkoxylated fatty alcohols and amine oxide surfactants. In some examples, the cleaning compositions may contain an ethoxylated nonionic surfactant. The nonionic surfactant may be selected from the ethoxylated alcohols and ethoxylated alkyl phenols of the formula $R(OC_2H_4)_nOH$, wherein R is selected from the group consisting of aliphatic hydrocarbon radicals containing from about 8 to about 17 carbon atoms and alkyl phenyl radicals in which the alkyl groups contain from about 8 to about 12 carbon atoms, and the average value of n is from about 5 to about 15. In one example, the nonionic surfactant is selected from ethoxylated alcohols having an average of about 24 carbon atoms in the alcohol and an average degree of ethoxylation of about 9 moles of ethylene oxide per mole of alcohol.

Other non-limiting examples of nonionic surfactants useful herein include: $C_8$-$C_{18}$ alkyl ethoxylates, such as, NEODOL® nonionic surfactants from Shell; $C_6$-$C_{12}$ alkyl phenol alkoxylates where the alkoxylate units may be ethyleneoxy units, propyleneoxy units, or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols, alkylpolysaccharides, polyhydroxy fatty acid amides and ether capped poly(oxyalkylated) alcohol surfactants.

Suitable nonionic detersive surfactants also include alkyl polyglucoside and alkyl alkoxylated alcohol. Suitable nonionic surfactants also include those sold under the tradename Lutensol® from BASF.

In some aspects, the nonionic surfactant is selected from alkyl alkoxylated alcohols, such as a $C_{8-18}$ alkyl alkoxylated alcohol, for example, a $C_{8-18}$ alkyl ethoxylated alcohol. The alkyl alkoxylated alcohol may have an average degree of alkoxylation of from about 1 to about 50, or from about 1 to about 30, or from about 1 to about 20, or from about 1 to about 10. In certain aspects, the alkyl alkoxylated alcohol is a $C_{8-18}$ alkyl ethoxylated alcohol having an average degree of ethoxylation of from about 1 to about 10, or from about 1 to about 7, or from about 1 to about 5, or from about 3 to about 7. The alkyl alkoxylated alcohol can be linear or branched, substituted or unsubstituted.

Cationic Surfactants

In some examples, the additional surfactant comprises one or more cationic surfactants.

In certain aspects, the detergent composition comprises from about 0.1% to about 10%, by weight of the composition, of an additional surfactant selected from one or more cationic surfactants. In certain aspects, the detergent composition comprises from about 0.1% to about 7%, by weight of the composition, of an additional surfactant selected from one or more cationic surfactants. In further aspects, the detergent composition comprises from about 0.3% to about 5%, by weight of the composition, of an additional surfactant selected from one or more cationic surfactants. In some aspects, the cleaning compositions of the invention are substantially free of cationic surfactants and surfactants that become cationic below a pH of 7 or below a pH of 6.

Non-limiting examples of cationic surfactants include: the quaternary ammonium surfactants, which can have up to 26 carbon atoms include: alkoxylate quaternary ammonium (AQA) surfactants, dimethyl hydroxyethyl lauryl ammonium chloride; polyamine cationic surfactants; cationic ester surfactants and amino surfactants, specifically amido propyldimethyl amine (APA) and/or trimethylammonium C8-16 alkyl salt.

Suitable cationic detersive surfactants also include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula:

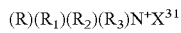

wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anions include: halides, for example chloride; sulphate; and sulphonate. Suitable cationic detersive surfactants are mono-$C_{6-18}$ alkyl mono-hydroxyethyl di-methyl quaternary ammonium chlorides. Highly suitable cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Zwitterionic Surfactants

Examples of zwitterionic surfactants include: derivatives of secondary and tertiary amines, derivatives of heterocyclic secondary and tertiary amines, or derivatives of quaternary ammonium, quaternary phosphonium or tertiary sulfonium compounds. Specific examples include $C_8$ to $C_{18}$ (for example from $C_{12}$ to $C_{18}$) amine oxides and sulfo and hydroxy betaines, such as N-alkyl-N,N-dimethylammino-1-propane sulfonate where the alkyl group can be $C_8$ to $C_{18}$ and in certain embodiments from $C_{10}$ to $C_{14}$.

Amphoteric Surfactants

Examples of amphoteric surfactants include aliphatic derivatives of secondary or tertiary amines, or aliphatic derivatives of heterocyclic secondary and tertiary amines in which the aliphatic radical may be straight or branched-chain and where one of the aliphatic substituents contains at least about 8 carbon atoms, typically from about 8 to about 18 carbon atoms, and at least one of the aliphatic substituents contains an anionic water-solubilizing group, e.g. carboxy, sulfonate, sulfate. Examples of compounds falling within this definition are sodium 3-(dodecylamino)propionate, sodium 3-(dodecylamino) propane-1-sulfonate, sodium 2-(dodecylamino)ethyl sulfate, sodium 2-(dimethylamino) octadecanoate, disodium 3-(N-carboxymethyldodecylamino)propane 1-sulfonate, disodium octadecyl-imminodiacetate, sodium 1-carboxymethyl-2-undecylimidazole, and sodium N,N-bis (2-hydroxyethyl)-2-sulfato-3-dodecoxypropylamine. Suitable amphoteric surfactants also include sarcosinates, glycinates, taurinates, and mixtures thereof.

Branched Surfactants

In some examples, the surfactant may be a branched surfactant, Suitable branched surfactants include anionic branched surfactants selected from branched sulphate or branched sulphonate surfactants, e.g., branched alkyl sulphate, branched alkyl alkoxylated sulphate, and branched alkyl benzene sulphonates, comprising one or more random alkyl branches, e.g., $C_{1-4}$ alkyl groups, typically methyl and/or ethyl groups.

In some aspects, the branched detersive surfactant is a mid-chain branched detersive surfactant, typically, a mid-chain branched anionic detersive surfactant, for example, a mid-chain branched alkyl sulphate and/or a mid-chain branched alkyl benzene sulphonate. In some aspects, the detersive surfactant is a mid-chain branched alkyl sulphate.

In some aspects, the mid-chain branches are $C_{1-4}$ alkyl groups, typically methyl and/or ethyl groups.

Enzymes

The cleaning compositions described herein may comprise one or more enzymes which provide cleaning performance and/or fabric care benefits. Examples of suitable enzymes include, but are not limited to, hemicellulases, peroxidases, proteases, cellulases, xylanases, lipases, xyloglucanase, phospholipases, esterases, cutinases, pectinases, mannanases, pectate lyases, keratinases, reductases, oxidases, phenoloxidases, lipoxygenases, ligninases, pullulanases, tannases, pentosanases, malanases,β-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in a detergent composition, the aforementioned additional enzymes may be present at levels from about 0.00001% to about 2%, from about 0.0001% to about 1% or even from about 0.001% to about 0.5% enzyme protein by weight of the detergent composition.

In one aspect preferred enzymes would include a protease. Suitable proteases include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus, B. alkalophilus, B. subtilis, B. amyloliquefaciens, Bacillus pumilus* and *Bacillus gibsonii*.

(b) trypsin-type or chymotrypsin-type proteases, such as trypsin (e.g., of porcine or bovine origin), including the Fusarium protease.

(c) metalloproteases, including those derived from *Bacillus amyloliquefaciens* Preferred proteases include those derived from *Bacillus gibsonii* or *Bacillus Lentus*.

Suitable commercially available protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark), those sold under the tradename Maxatase®, Maxacal®, Maxapem®, Properase®, Purafect®, Purafect Prime®, Purafect Ox®, FN3®, FN4®, Excellase® and Purafect OXP® by Genencor International, those sold under the tradename Opticlean® and Optimase® by Solvay Enzymes, those available from Henkel/Kemira, namely BLAP (sequence shown in FIG. 29 of U.S. Pat. No. 5,352,604 with the folowing mutations S99D+S101 R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D)– all from Henkel/Kemira; and KAP (*Bacillus alkalophilus subtilisin* with mutations A230V+S256G+S259N) from Kao.

Suitable alpha-amylases include those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCIB 12289, NCIB 12512, NCIB 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) the variants with substitutions in one or more of the following positions versus the enzyme listed as SEQ ID No. 2 in WO 96/23874: 15, 23, 105, 106, 124, 128, 133, 154, 156, 181, 188, 190, 197, 202, 208, 209, 243, 264, 304, 305, 391, 408, and 444.

(b) the variants with one or more substitutions in the following positions versus the AA560 enzyme listed as SEQ ID No. 12:

26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(c) variants exhibiting at least 90% identity with SEQ ID No. 4 in WO06/002643, the wild-type enzyme from *Bacillus SP*722, especially variants with deletions in the 183 and 184 positions and variants described in WO 00/60060, which is incorporated herein by reference.

(d) variants exhibiting at least 95% identity with the wild-type enzyme from *Bacillus* sp.707 (SEQ ID NO:7 in U.S. Pat. No. 6,093, 562), especially those comprising one or more of the following mutations M202, M208, S255, R172, and/or M261. Preferably said amylase comprises one or more of M202L, M202V, M2025, M202T, M2021, M202Q, M202W, S255N and/or R172Q. Particularly preferred are those comprising the M202L or M202T mutations.

(e) variants described in WO 09/149130, preferably those exhibiting at least 90% identity with SEQ ID NO: 1 or SEQ ID NO:2 in WO 09/149130, the wild-type enzyme from *Geobacillus Stearophermophilus* or a truncated version thereof.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE® and PURASTAR OXAM® (Genencor International Inc., Palo Alto, Calif.) and KAM® (Kao, 14-10 Nihonbashi Kayabacho, 1-chome, Chuo-ku Tokyo 103-8210, Japan). In one aspect, suitable amylases include NATALASE®, STAINZYME® and STAINZYME PLUS® and mixtures thereof.

In one aspect, such enzymes may be selected from the group consisting of: lipases, including "first cycle lipases". In one aspect, the lipase is a first-wash lipase, preferably a variant of the wild-type lipase from *Thermomyces lanuginosus* comprising one or more of the T231R and N233R mutations. The wild-type sequence is the 269 amino acids (amino acids 23-291) of the Swissprot accession number Swiss-Prot O59952 (derived from *Thermomyces lanuginosus* (*Humicola lanuginosa*)). Preferred lipases would include those sold under the tradenames Lipex® and Lipolex®.

In one aspect, other preferred enzymes include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403B2) and mixtures thereof. Suitable endoglucanases are sold under the tradenames Celluclean® and Whitezyme® (Novozymes A/S, Bagsvaerd, Denmark).

Other preferred enzymes include pectate lyases sold under the tradenames Pectawash®, Pectaway®, Xpect® and mannanases sold under the tradenames Mannaway® (all from Novozymes A/S, Bagsvaerd, Denmark), and Purabrite® (Genencor International Inc., Palo Alto, Calif.).

Enzyme Stabilizing System

The enzyme-containing compositions described herein may optionally comprise from about 0.001% to about 10%, in some examples from about 0.005% to about 8%, and in other examples, from about 0.01% to about 6%, by weight of the composition, of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, chlorine bleach scavengers and mixtures thereof, and are designed to address different stabilization problems depending on the type and physical form of the cleaning composition. In the case of aqueous detergent compositions comprising protease, a reversible protease inhibitor, such as a boron compound, including borate, 4-formyl phenylboronic acid, phenylboronic acid and derivatives thereof, or compounds such as calcium formate, sodium formate and 1,2-propane diol may be added to further improve stability.

Builders

The cleaning compositions of the present invention may optionally comprise a builder. Built cleaning compositions typically comprise at least about 1% builder, based on the total weight of the composition. Liquid cleaning compositions may comprise up to about 10% builder, and in some examples up to about 8% builder, of the total weight of the composition. Granular cleaning compositions may comprise up to about 30% builder, and in some examples up to about 5% builder, by weight of the composition.

Builders selected from aluminosilicates (e.g., zeolite builders, such as zeolite A, zeolite P, and zeolite MAP) and silicates assist in controlling mineral hardness in wash water, especially calcium and/or magnesium, or to assist in the removal of particulate soils from surfaces. Suitable builders may be selected from the group consisting of phosphates, such as polyphosphates (e.g., sodium tri-polyphosphate), especially sodium salts thereof; carbonates, bicarbonates, sesquicarbonates, and carbonate minerals other than sodium carbonate or sesquicarbonate; organic mono-, di-, tri-, and tetracarboxylates, especially water-soluble nonsurfactant carboxylates in acid, sodium, potassium or alkanolammonium salt form, as well as oligomeric or water-soluble low molecular weight polymer carboxylates including aliphatic and aromatic types; and phytic acid. These may be complemented by borates, e.g., for pH-buffering purposes, or by sulfates, especially sodium sulfate and any other fillers or carriers which may be important to the engineering of stable surfactant and/or builder-containing cleaning compositions. Additional suitable builders may be selected from citric acid, lactic acid, fatty acid, polycarboxylate builders, for example, copolymers of acrylic acid, copolymers of acrylic acid and maleic acid, and copolymers of acrylic acid and/or maleic acid, and other suitable ethylenic monomers with various types of additional functionalities. Also suitable for use as builders herein are synthesized crystalline ion exchange materials or hydrates thereof having chain structure and a composition represented by the following general anhydride form: $x(M_2O).ySiO_2.zM'O$ wherein M is Na and/or K, M' is Ca and/or Mg; y/x is 0.5 to 2.0; and z/x is 0.005 to 1.0

Alternatively, the composition may be substantially free of builder.

Structurant/Thickeners i. Di-benzylidene Polyol Acetal Derivative

The fluid detergent composition may comprise from about 0.01% to about 1% by weight of a dibenzylidene polyol acetal derivative (DBPA), or from about 0.05% to about 0.8%, or from about 0.1% to about 0.6%, or even from about 0.3% to about 0.5%. Non-limiting examples of suitable DBPA molecules are disclosed in U.S. 61/167604. In one aspect, the DBPA derivative may comprise a dibenzylidene sorbitol acetal derivative (DBS). Said DBS derivative may be selected from the group consisting of: 1,3:2,4-dibenzylidene sorbitol; 1,3:2,4-di(p-methylbenzylidene) sorbitol; 1,3:2,4-di(p-chlorobenzylidene) sorbitol; 1,3:2,4-di(2,4-dimethyldibenzylidene) sorbitol; 1,3:2,4-di(p-ethylbenzylidene) sorbitol; and 1,3:2,4-di(3,4-dimethyldibenzylidene) sorbitol or mixtures thereof.

ii. Bacterial Cellulose

The fluid detergent composition may also comprise from about 0.005% to about 1% by weight of a bacterial cellulose network. The term "bacterial cellulose" encompasses any type of cellulose produced via fermentation of a bacteria of the genus *Acetobacter* such as CELLULON® by CPKelco U.S. and includes materials referred to popularly as microfibrillated cellulose, reticulated bacterial cellulose, and the like. In one aspect, said fibres have cross sectional dimensions of 1.6 nm to 3.2 nm by 5.8 nm to 133 nm. Additionally, the bacterial cellulose fibres have an average microfibre length of at least about 100 nm, or from about 100 to about 1,500 nm. In one aspect, the bacterial cellulose microfibres have an aspect ratio, meaning the average microfibre length divided by the widest cross sectional microfibre width, of from about 100:1 to about 400:1, or even from about 200:1 to about 300:1.

iii. Coated Bacterial Cellulose

In one aspect, the bacterial cellulose is at least partially coated with a polymeric thickener. In one aspect the at least partially coated bacterial cellulose comprises from about 0.1% to about 5%, or even from about 0.5% to about 3%, by weight of bacterial cellulose; and from about 10% to about 90% by weight of the polymeric thickener. Suitable bacterial cellulose may include the bacterial cellulose described above and suitable polymeric thickeners include: carboxymethylcellulose, cationic hydroxymethylcellulose, and mixtures thereof.

iv. Cellulose Fibers Non-bacterial Cellulose Derived

In one aspect, the composition may further comprise from about 0.01 to about 5% by weight of the composition of a cellulosic fiber. Said cellulosic fiber may be extracted from vegetables, fruits or wood. Commercially available examples are Avicel® from FMC, Citri-Fi from Fiberstar or Betafib from Cosun.

v. Non-Polymeric Crystalline Hydroxyl-Functional Materials

In one aspect, the composition may further comprise from about 0.01 to about 1% by weight of the composition of a non-polymeric crystalline, hydroxyl functional structurant. Said non-polymeric crystalline, hydroxyl functional structurants generally may comprise a crystallizable glyceride which can be pre-emulsified to aid dispersion into the final fluid detergent composition. In one aspect, crystallizable glycerides may include hydrogenated castor oil or "HCO" or derivatives thereof, provided that it is capable of crystallizing in the liquid detergent composition.

vi. Polymeric Structuring Agents

Fluid detergent compositions of the present invention may comprise from about 0.01% to about 5% by weight of a naturally derived and/or synthetic polymeric structurant. Examples of naturally derived polymeric structurants of use in the present invention include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. Examples of synthetic polymeric structurants of use in the present invention include: polycarboxylates, polyacrylates, hydrophobically modified ethoxylated urethanes, hydrophobically modified non-ionic polyols and mixtures thereof. In one aspect, said polycarboxylate polymer is a polyacrylate, polymethacrylate or mixtures thereof. In another aspect, the polyacrylate is a copolymer of unsaturated mono- or di-carbonic acid and $C_1$-$C_{30}$ alkyl ester of the (meth)acrylic acid. Said copolymers are available from Noveon inc under the tradename Carbopol Aqua 30.

vii. Di-amido-gellants

In one aspect, the external structuring system may comprise a di-amido gellant having a molecular weight from about 150 g/mol to about 1,500 g/mol, or even from about 500 g/mol to about 900 g/mol. Such di-amido gellants may comprise at least two nitrogen atoms, wherein at least two of said nitrogen atoms form amido functional substitution groups. In one aspect, the amido groups are different. In another aspect, the amido functional groups are the same. Non-limiting examples of useful di-amido gellants are: N,N'-(2S,2'S)-1,1'-(dodecane-1,12-diylbis(azanediyl))bis(3-methyl-1-oxobutane-2,1-diyl) diisonicotinamide; dibenzyl (2S,2'S)-1,1'-(propane-1,3-diylbis(azanediyl))bis(3-methyl-1-oxobutane-2,1-diyl)dicarbamate; and dibenzyl (2S,2'S)-1,1'-(dodecane-1,12-diylbis (azanediyl))bis(1-oxo-3-phenyl-propane-2,1-diyl)dicarbamate.

Polymeric Dispersing Agents

The detergent composition may comprise one or more polymeric dispersing agents. Examples are carboxymethylcellulose, poly(vinyl-pyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The detergent composition may comprise one or more amphiphilic cleaning polymers such as the compound having the following general structure: bis(($C_2H_5$O)($C_2H_4$O)n) ($CH_3$)—$N^+$—$C_xH_{2x}$—$N^+$—($CH_3$)-bis(($C_2H_5$O)($C_2H_4$O)n), wherein n=from 20 to 30, and x=from 3 to 8, or sulphated or sulphonated variants thereof.

The detergent composition may comprise amphiphilic alkoxylated grease cleaning polymers which have balanced hydrophilic and hydrophobic properties such that they remove grease particles from fabrics and surfaces. Specific embodiments of the amphiphilic alkoxylated grease cleaning polymers of the present invention comprise a core structure and a plurality of alkoxylate groups attached to that core structure. These may comprise alkoxylated polyalkyleneimines, for example, having an inner polyethylene oxide block and an outer polypropylene oxide block. Such compounds may include, but are not limited to, ethoxylated polyethyleneimine, ethoxylated hexamethylene diamine, and sulfated versions thereof. Polypropoxylated derivatives may also be included. A wide variety of amines and polyalklyeneimines can be alkoxylated to various degrees. A useful example is 600 g/mol polyethyleneimine core ethoxylated to 20 EO groups per NH and is available from BASF. The cleaning compositions described herein may comprise from about 0.1% to about 10%, and in some examples, from about 0.1% to about 8%, and in other examples, from about 0.1% to about 6%, by weight of the cleaning composition, of alkoxylated polyamines.

Alkoxylated polycarboxylates such as those prepared from polyacrylates are useful herein to provide additional grease removal performance. Chemically, these materials comprise polyacrylates having one ethoxy side-chain per every 7-8 acrylate units. The side-chains are of the formula —($CH_2CH_2$O)$_m$($CH_2$)$_n$$CH_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. The detergent compositions described herein may comprise from about 0.1% to about 10%, and in some examples, from about 0.25% to about 5%, and in other examples, from about 0.3% to about 2%, by weight of the cleaning composition, of alkoxylated polycarboxylates.

Suitable amphilic graft co-polymer preferable include the amphilic graft co-polymer comprises (i) polyethyelene glycol backbone; and (ii) and at least one pendant moiety selected from polyvinyl acetate, polyvinyl alcohol and mixtures thereof. A preferred amphilic graft co-polymer is Sokalan® HP22, supplied from BASF. Suitable polymers include random graft copolymers, preferably a polyvinyl acetate grafted polyethylene oxide copolymer having a polyethylene oxide backbone and multiple polyvinyl acetate side chains. The molecular weight of the polyethylene oxide backbone is typically about 6000 and the weight ratio of the polyethylene oxide to polyvinyl acetate is about 40 to 60 and no more than 1 grafting point per 50 ethylene oxide units.

Carboxylate polymer—The detergent compositions of the present invention may also include one or more carboxylate polymers such as a maleate/acrylate random copolymer or polyacrylate homopolymer. In one aspect, the carboxylate polymer is a polyacrylate homopolymer having a molecular weight of from 4,000 Da to 9,000 Da, or from 6,000 Da to 9,000 Da.

Soil release polymer—The detergent compositions of the present invention may also include one or more soil release polymers having a structure as defined by one of the following structures (III), (IV) or (V):

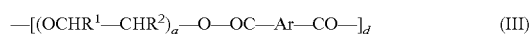

$$—[(OCHR^1—CHR^2)_a—O—OC—Ar—CO—]_d \quad (III)$$

$$—[(OCHR^3—CHR^4)_b—O—OC\text{-sAr}—CO—]_e \quad (IV)$$

$$—[(OCHR^5—CHR^6)_c—OR^7]_f \quad (V)$$

wherein:
a, b and c are from 1 to 200;
d, e and f are from 1 to 50;
Ar is a 1,4-substituted phenylene;
sAr is 1,3-substituted phenylene substituted in position 5 with $SO_3$Me;
Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;
$R^1$, $R^2$, $R^3$, $R^4$, $R^5$ and $R^6$ are independently selected from H or $C_1$-$C_{18}$ n- or iso-alkyl; and $R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN300 and SRN325 supplied by Clamant. Other suitable soil release polymers are Marloquest polymers, such as Marloquest SL supplied by Sasol.

Cellulosic polymer—The consumer products of the present invention may also include one or more cellulosic polymers including those selected from alkyl cellulose, alkyl alkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixtures thereof. In one aspect, the carboxymethyl cellulose has a degree of carboxymethyl substitution from 0.5 to 0.9 and a molecular weight from 100,000 Da to 300,000 Da.

Amines

Various amines may be used in the cleaning compositions described herein for added removal of grease and particulates from soiled materials. The detergent compositions described herein may comprise from about 0.1% to about 10%, in some examples, from about 0.1% to about 4%, and in other examples, from about 0.1% to about 2%, by weight of the cleaning composition, of additional amines. Non-limiting examples of amines include, but are not limited to, polyamines, oligoamines, triamines, diamines, pentamines, tetraamines, polyetheramines, or combinations thereof. Specific examples of suitable additional amines include tetraethylenepentamine, triethylenetetraamine, diethylenetriamine, polyetheramines, or a mixture thereof. In one aspect, The compositions described herein may comprise a polyetheramine for added removal of grease and particulates from soiled materials. In one aspect, the compositions described herein may comprise from about 0.1% to about 10%, in some examples, from about 0.1% to about 6% or from about 0.2% to about 5% or from about 0.1% to about 2%, and in other examples, from about 0.5% to about 3% by weight of the cleaning composition, of a polyetheramine.

A suitable polyetheramine is represented by the structure of Formula (VI):

about 200, typically about 2 to about 20 or about 3 to about 20, more typically about 2 to about 10 or about 3 to about 8 or about 4 to about 6, where x≥1 and y≥1, and the sum of $x_1+y_1$ is in the range of about 2 to about 200, typically about 2 to about 20 or about 3 to about 20, more typically about 2 to about 10 or about 3 to about 8 or about 2 to about 4, where $x_1$≥1 and $y_1$≥1.

Another suitable polyetheramine is represented by the structure of Formula (VII):

Formula (II)

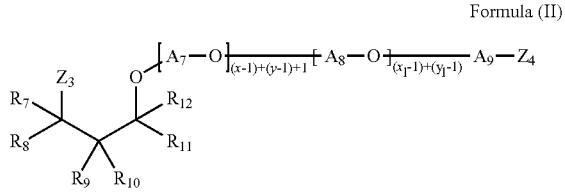

where each of $R_7$-$R_{12}$ is independently selected from H, alkyl, cycloalkyl, aryl, alkylaryl, or arylalkyl, where at least one of $R_7$-$R_{12}$ is different from H, typically at least one of $R_7$-$R_{12}$ is an alkyl group having 2 to 8 carbon atoms, each of $A_7$-$A_9$ is independently selected from linear or branched alkylenes having 2 to 18 carbon atoms, typically 2 to 10 carbon atoms, more typically, 2 to 5 carbon atoms, each of $Z_3$-$Z_4$ is independently selected from OH or $NH_2$, where at least one of $Z_3$-$Z_4$ is $NH_2$, typically each of $Z_3$ and $Z_4$ is $NH_2$, where the sum of x+y is in the range of about 2 to about 200, typically about 2 to about 20 or about 3 to about 20, more typically about 2 to about 10 or about 3 to about 8 or about 2 to about 4, where x≥1 and y≥1, and the sum of $x_1+y_1$ is in the range of about 2 to about 200, typically about 2 to about 20 or about 3 to about 20, more typically about 2 to about 10 or about 3 to about 8 or about 2 to about 4, where $x_1$≥1 and $y_1$≥1.

Another suitable polyetheramine is represented by the structure of Formula VIII:

Formula (III)

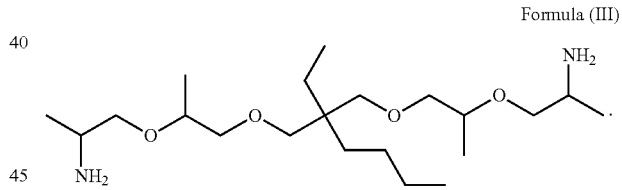

Formula (VI)

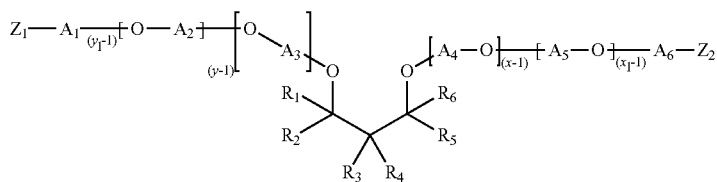

where each of $R_1$-$R_6$ is independently selected from H, alkyl, cycloalkyl, aryl, alkylaryl, or arylalkyl, where at least one of $R_1$-$R_6$ is different from H, typically at least one of $R_1$-$R_6$ is an alkyl group having 2 to 8 carbon atoms, each of $A_1$-$A_6$ is independently selected from linear or branched alkylenes having 2 to 18 carbon atoms, typically 2 to 10 carbon atoms, more typically, 2 to 5 carbon atoms, each of $Z_1$-$Z_2$ is independently selected from OH or $NH_2$, where at least one of $Z_1$-$Z_2$ is $NH_2$, typically each of $Z_1$ and $Z_2$ is $NH_2$, where the sum of x+y is in the range of about 2 to Solvents—suitable solvents include, but are not limited to, water, alcohol, paraffins, glycols, glycerols, and mixtures thereof. Bleaching Agents—The detergent compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the detergent compositions of the present invention may comprise from about 0.1% to about 50% or even from about 0.1% to about 25% bleaching agent by weight of the detergent composition. Examples of suitable bleaching agents include:

(1) photobleaches for example sulfonated zinc phthalocyanine, sulfonated aluminum phthalocyanine, xanthene dyes and mixtures thereof;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxone®, and mixtures thereof. Suitable percarboxylic acids include hydrophobic and hydrophilic peracids having the formula R—(C=O)O—O—M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or from 1 to 30 wt % of the overall fabric and home care product and are typically incorporated into such fabric and home care products as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (4) bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). While any suitable bleach activator may be employed, in one aspect the subject composition may comprise NOBS, TAED or mixtures thereof.

When present, the peracid and/or bleach activator is generally present in the detergent composition in an amount of from about 0.1 to about 60 wt %, from about 0.5 to about 40 wt % or even from about 0.6 to about 10 wt % based on the fabric and home care product. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Bleach Catalysts—The detergent compositions of the present invention may also include one or more bleach catalysts capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

In another aspect, the laundry detergent composition comprises a bleach ingredient, the bleach ingredient have a $\log P_{o/w}$ no greater than 0, no greater than −0.5, no greater than −1.0, no greater than −1.5, no greater than −2.0, no greater than −2.5, no greater than −3.0, or even no greater than −3.5. The method for determining $\log P_{o/w}$ is described in more detail below.

Typically, the bleach ingredient is capable of generating a bleaching species having a $X_{SO}$ of from 0.01 to about 0.30, from 0.05 to about 0.25, or even from about 0.10 to 0.20. The method for determining $X_{SO}$ is described in more detail below. For example, bleaching ingredients having an isoquinolinium structure are capable of generating a bleaching species that has an oxaziridinium structure. In this example, the $X_{SO}$ is that of the oxaziridinium bleaching species.

In one aspect, the bleach catalyst has a structure corresponding to general formula below:

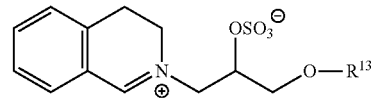

wherein $R^{13}$ is selected from the group consisting of 2-ethylhexyl, 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl;

Log $P_{o/w}$ is determined according to the method found in Brooke, D. N., Dobbs, A. J., Williams, N, *Ecotoxicology and Environmental Safety* (1986) 11(3): 251-260. The parameter $X_{SO}$ is determined according to the method described in Adam, W., Haas, W., Lohray, B. B. *Journal of the American Chemical Society* (1991) 113(16) 6202-6208.

Brighteners

Optical brighteners or other brightening or whitening agents may be incorporated at levels of from about 0.01% to about 1.2%, by weight of the composition, into the cleaning compositions described herein. Commercial fluorescent brighteners suitable for the present invention can be classified into subgroups, including but not limited to: derivatives of stilbene, pyrazoline, coumarin, benzoxazoles, carboxylic acid, methinecyanines, dibenzothiophene-5,5-dioxide, azoles, 5- and 6-membered-ring heterocycles, and other miscellaneous agents.

In some examples, the fluorescent brightener herein comprises a compound of formula (IX):

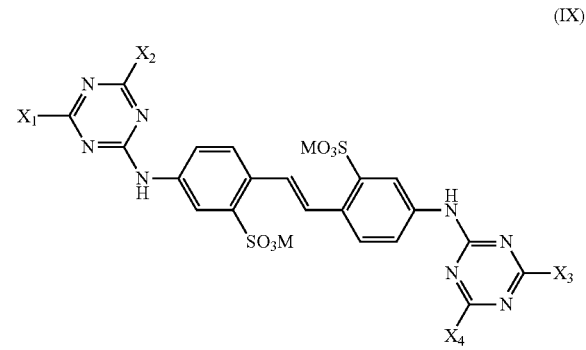

wherein: $X_1$, $X_2$, $X_3$, and $X_4$ are —$N(R^1)R^2$, wherein $R^1$ and $R^2$ are independently selected from a hydrogen, a phenyl, hydroxyethyl, or an unsubstituted or substituted $C_1$-$C_8$ alkyl, or —$N(R^1)R^2$ form a heterocyclic ring, preferably $R^1$ and $R^2$ are independently selected from a hydrogen or phenyl, or —$N(R^1)R^2$ form a unsubstituted or substituted morpholine ring; and M is a hydrogen or a cation, preferably M is sodium or potassium, more preferably M is sodium.

In some examples, the fluorescent brightener is selected from the group consisting of disodium 4,4'-bis {[4-anilino-6-morpholino-s-triazin-2-yl]-amino}-2,2'-stilbenedisulfonate (brightener 15, commercially available under the tradename Tinopal AMS-GX by Ciba Geigy Corporation), disodium4,4'-bis {[4-anilino-6-(N-2-bis-hydroxyethyl)-s-triazine-2-yl]-amino}-2,2'-stilbenedisulonate (commercially available under the tradename Tinopal UNPA-GX by Ciba-Geigy Corporation), disodium 4,4'-bis {[4-anilino-6-(N-2-hydroxyethyl-N-methylamino)-s-triazine-2-yl-]amino}-2, 2'-stilbenedisulfonate (commercially available under the tradename Tinopal 5BM-GX by Ciba-Geigy Corporation). More preferably, the fluorescent brightener is disodium 4,4'-bis {[4-anilino-6-morpholino-s-triazin-2-yl]-amino}-2, 2'-stilbenedisulfonate. The brighteners may be added in particulate form or as a premix with a suitable solvent, for example nonionic surfactant, monoethanolamine, propane diol.

Suds Suppressor

The cleaning compositions herein may comprise from 0.1% to about 10%, by weight of the composition, of an additional suds suppressor. When utilized as suds suppressors, monocarboxylic fatty acids, and salts thereof, may be present in amounts of up to about 5% by weight of the cleaning composition, and in some examples, from about 0.5% to about 3% by weight of the cleaning composition. Additional silicone suds suppressors may be utilized in amounts of up to about 2.0% by weight of the cleaning composition, although higher amounts may be used. Monostearyl phosphate suds suppressors may be utilized in amounts ranging from about 0.1% to about 2% by weight of the cleaning composition. Hydrocarbon suds suppressors may be utilized in amounts ranging from about 0.01% to about 5.0% by weight of the cleaning composition, although higher levels can be used. Alcohol suds suppressors may be used at a concentration ranging from about 0.2% to about 3% by weight of the cleaning composition.

Water-Soluble Film

The compositions of the present invention may also be encapsulated within a water-soluble film. Preferred film materials are preferably polymeric materials. The film material can, for example, be obtained by casting, blow-moulding, extrusion or blown extrusion of the polymeric material, as known in the art.

Preferred polymers, copolymers or derivatives thereof suitable for use as pouch material are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof. Preferably, the level of polymer in the pouch material, for example a PVA polymer, is at least 60%. The polymer can have any weight average molecular weight, preferably from about 1000 Da to 1,000,000 Da, more preferably from about 10,000 Da to 300,000 Da yet more preferably from about 20,000 Da to 150,000 Da. Mixtures of polymers can also be used as the pouch material. Naturally, different film material and/or films of different thickness may be employed in making the compartments of the present invention. A benefit in selecting different films is that the resulting compartments may exhibit different solubility or release characteristics.

Most preferred film materials are PVA films known under the MonoSol trade reference M8630, M8900, H8779.

The film material herein can also comprise one or more additive ingredients. For example, it can be beneficial to add plasticisers, for example glycerol, ethylene glycol, diethyleneglycol, propylene glycol, sorbitol and mixtures thereof. Other additives include functional detergent additives to be delivered to the wash water, for example organic polymeric dispersants.

Suds Boosters

If high sudsing is desired, suds boosters such as the $C_{10}$-$C_{16}$ alkanolamides may be incorporated into the cleaning compositions at a concentration ranging from about 1% to about 10% by weight of the cleaning composition. Some examples include the $C_{10}$-$C_{14}$ monoethanol and diethanol amides. If desired, water-soluble magnesium and/or calcium salts such as $MgCl_2$, $MgSO_4$, $CaCl_2$, $CaSO_4$, and the like, may be added at levels of about 0.1% to about 2% by weight of the cleaning composition, to provide additional suds and to enhance grease removal performance.

Fabric Hueing Agents

The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Direct, Basic, Reactive or hydrolysed Reactive, Solvent or Disperse dyes for example that are classified as Blue, Violet, Red, Green or Black, and provide the desired shade either alone or in combination. In another aspect, suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes and mixtures thereof. In another aspect, suitable small molecule dyes include small molecule dyes selected from the group consisting of C. I. numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof.

In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used).

Encapsulates

The compositions may comprise an encapsulate. In some aspects, the encapsulate comprises a core, a shell having an inner and outer surface, where the shell encapsulates the core.

In certain aspects, the encapsulate comprises a core and a shell, where the core comprises a material selected from perfumes; brighteners; dyes; insect repellants; silicones; waxes; flavors; vitamins; fabric softening agents; skin care agents, e.g., paraffins; enzymes; anti-bacterial agents; bleaches; sensates; or mixtures thereof; and where the shell comprises a material selected from polyethylenes; polyamides; polyvinylalcohols, optionally containing other co-monomers; polystyrenes; polyisoprenes; polycarbonates; polyesters; polyacrylates; polyolefins; polysaccharides, e.g., alginate and/or chitosan; gelatin; shellac; epoxy resins; vinyl polymers; water insoluble inorganics; silicone; aminoplasts, or mixtures thereof. In some aspects, where the shell comprises an aminoplast, the aminoplast comprises polyurea, polyurethane, and/or polyureaurethane. The polyurea may comprise polyoxymethyleneurea and/or melamine formaldehyde.

In some aspects, the encapsulate comprises a core, and the core comprises a perfume. In certain aspects, the encapsulate comprises a shell, and the shell comprises melamine formaldehyde and/or cross linked melamine formaldehyde. In some aspects, the encapsulate comprises a core comprising a perfume and a shell comprising melamine formaldehyde and/or cross linked melamine formaldehyde Suitable encapsulates may comprise a core material and a shell, where the shell at least partially surrounds the core material. At least 75%, or at least 85%, or even at least 90% of the encapsulates may have a fracture strength of from about 0.2 MPa to about 10 MPa, from about 0.4 MPa to about 5MPa, from about 0.6 MPa to about 3.5 MPa, or even from about 0.7 MPa to about 3MPa; and a benefit agent leakage of from 0% to about 30%, from 0% to about 20%, or even from 0% to about 5%.

In some aspects, at least 75%, 85% or even 90% of said encapsulates may have a particle size of from about 1 microns to about 80 microns, about 5 microns to 60 microns, from about 10 microns to about 50 microns, or even from about 15 microns to about 40 microns.

In some aspects, at least 75%, 85% or even 90% of said encapsulates may have a particle wall thickness of from about 30 nm to about 250 nm, from about 80 nm to about 180 nm, or even from about 100 nm to about 160 nm.

In some aspects, the core of the encapsulate comprises a material selected from a perfume raw material and/or optionally a material selected from vegetable oil, including neat and/or blended vegetable oils including caster oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaphthalene, petroleum spirits, including kerosene, mineral oil or mixtures thereof; aromatic solvents, including benzene, toluene or mixtures thereof; silicone oils; or mixtures thereof.

In some aspects, the wall of the encapsulate comprises a suitable resin, such as the reaction product of an aldehyde and an amine. Suitable aldehydes include formaldehyde. Suitable amines include melamine, urea, benzoguanamine, glycoluril, or mixtures thereof. Suitable melamines include methylol melamine, methylated methylol melamine, imino melamine and mixtures thereof. Suitable ureas include, dimethylol urea, methylated dimethylol urea, urea-resorcinol, or mixtures thereof.

In some aspects, suitable formaldehyde scavengers may be employed with the encapsulates, for example, in a capsule slurry and/or added to a composition before, during, or after the encapsulates are added to such composition.

In addition, the materials for making the aforementioned encapsulates can be obtained from Solutia Inc. (St Louis, Mo. U.S.A.), Cytec Industries (West Paterson, N.J., U.S.A.), sigma-Aldrich (St. Louis, Mo. U.S.A.), CP Kelco Corp. of San Diego, Calif., USA; BASF AG of Ludwigshafen, Germany; Rhodia Corp. of Cranbury, N.J., USA; Hercules Corp. of Wilmington, Del., USA; Agrium Inc. of Calgary, Alberta, Canada, ISP of N.J., U.S.A., Akzo Nobel of Chicago, Ill, USA; Stroever Shellac Bremen of Bremen, Germany; Dow Chemical Company of Midland, Mass., USA; Bayer AG of Leverkusen, Germany; Sigma-Aldrich Corp., St. Louis, Mo., USA.

Perfumes in Addition to Organic Material

Perfumes and perfumery ingredients may be used in the cleaning compositions described herein. Non-limiting examples of perfume and perfumery ingredients include, but are not limited to, aldehydes, ketones, esters, and the like. Other examples include various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes may be included at a concentration ranging from about 0.01% to about 2% by weight of the cleaning composition.

Dye Transfer Inhibiting Agents

Fabric cleaning compositions may also include one or more materials effective for inhibiting the transfer of dyes from one fabric to another during the cleaning process. Generally, such dye transfer inhibiting agents may include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents may be used at a concentration of about 0.0001% to about 10%, by weight of the composition, in some examples, from about 0.01% to about 5%, by weight of the composition, and in other examples, from about 0.05% to about 2% by weight of the composition.

Chelating Agents

The detergent compositions described herein may also contain one or more metal ion chelating agents. Suitable molecules include copper, iron and/or manganese chelating agents and mixtures thereof. Such chelating agents can be selected from the group consisting of phosphonates, amino carboxylates, amino phosphonates, succinates, polyfunctionally-substituted aromatic chelating agents, 2-pyridinol-N-oxide compounds, hydroxamic acids, carboxymethyl inulins and mixtures thereof. Chelating agents can be present in the acid or salt form including alkali metal, ammonium, and substituted ammonium salts thereof, and mixtures thereof.

Aminocarboxylates useful as chelating agents include, but are not limited to ethylenediaminetetracetates (EDTA); N-(hydroxyethyl)ethylenediaminetriacetates (HEDTA); nitrilotriacetates (NTA); ethylenediamine tetraproprionates; triethylenetetraaminehexacetates, diethylenetriamine-pentaacetates (DTPA); methylglycinediacetic acid (MGDA); Glutamic acid diacetic acid (GLDA); ethanoldiglycines; triethylenetetraaminehexaacetic acid (TTHA); N-hydroxyethyliminodiacetic acid (HEIDA); dihydroxyethylglycine (DHEG); ethylenediaminetetrapropionic acid (EDTP) and derivatives thereof.

Phosphorus containing chelants include, but are not limited to diethylene triamine penta (methylene phosphonic acid) (DTPMP CAS 15827-60-8); ethylene diamine tetra (methylene phosphonic acid) (EDTMP CAS 1429-50-1); 2-Phosphonobutane 1,2,4-tricarboxylic acid (Bayhibit® AM); hexamethylene diamine tetra(methylene phosphonic acid) (CAS 56744-47-9); hydroxy-ethane diphosphonic acid (HEDP CAS 2809-21-4); hydroxyethane dimethylene phosphonic acid; 2-phosphono-1,2,4-Butanetricarboxylic acid (CAS 37971-36-1); 2-hydroxy-2-phosphono-Acetic acid (CAS 23783-26-8); Aminotri(methylenephosphonic acid) (ATMP CAS 6419-19-8); P,P'-(1,2-ethanediyl)bis-Phosphonic acid (CAS 6145-31-9); P,P'-methylenebis-Phosphonic acid (CAS 1984-15-2); Triethylenediaminetetra(methylene phosphonic acid) (CAS 28444-52-2); P-(1-hydroxy-1-methylethyl)-Phosphonic acid (CAS 4167-10-6); bis(hexamethylene triamine penta(methylenephosphonic acid)) (CAS 34690-00-1); N2,N2,N6,N6-tetrakis(phosphonomethyl)-Lysine (CAS 194933-56-7, CAS 172780-03-9), salts thereof, and mixtures thereof. Preferably, these aminophosphonates do not contain alkyl or alkenyl groups with more than about 6 carbon atoms.

A biodegradable chelator that may also be used herein is ethylenediamine disuccinate ("EDDS"). In some examples, but of course not limited to this particular example, the [S,S] isomer. In other examples, the trisodium salt of EDDA may be used, though other forms, such as magnesium salts, may also be useful. Polymeric chelants such as Trilon P® from BASF may also be useful.

Polyfunctionally-substituted aromatic chelating agents may also be used in the cleaning compositions. Compounds of this type in acid form are dihydroxydisulfobenzenes, such as 1,2-dihydroxy-3,5-disulfobenzene, also known as Tiron. Other sulphonated catechols may also be used. In addition to the disulfonic acid, the term "tiron" may also include mono- or di-sulfonate salts of the acid, such as, for example, the disodium sulfonate salt, which shares the same core molecular structure with the disulfonic acid.

The detergent composition according to the present invention may comprise a substituted or unsubstituted 2-pyridinol-N-oxide compound or a salt thereof, as a chelating agent. Included within the scope of this invention are tautomers of this compound, e.g., 1-Hydroxy-2(1H)-pyridinone, as chelating agents. In certain aspects, the detergent composition comprises a 2-pyridinol-N-oxide compound selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof. In certain aspects, the detergent composition comprises a 1-Hydroxy-2(1H)-pyridinone compound selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid,methyl ester (CAS 36979-78-9); 1-hydroxy-5-nitro -2(1H)-Pyridinone (CAS 45939-70-6); and mixtures thereof. These compounds are commercially available from, for example, Sigma-Aldrich (St. Louis, Mo.), Princeton Building Blocks (Monmouth Junction, N.J.), 3B Scientific Corporation (Libertyville, Ill.), SynFine Research (Richmond Hill, ON), Ryan Scientific, Inc. (Mt. Pleasant, S.C.), and/or Aces Pharma (Branford, Conn.).

Hydroxamic acids are a class of chemical compounds in which a hydroxylamine is inserted into a carboxylic acid and be used as chelating agents. The general structure of a hydroxamic acid is the following:

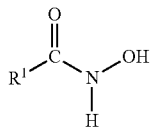

The preferred hydroxamates are those where $R^1$ is C4 to C14 alkyl, preferably normal alkyl, most preferably saturated, salts thereof and mixtures thereof. When the C8 material is used, it called octyl hydroxamic acid.

Other suitable chelating agents for use herein are the commercial DEQUEST series, and chelants from Monsanto, Akzo-Nobel, DuPont, Dow, the Trilon® series from BASF and Nalco.

The chelant may be present in the detergent compositions disclosed herein at from about 0.005% to about 15% by weight, about 0.01% to about 5% by weight, about 0.1% to about 3.0% by weight, or from about 0.2% to about 0.7% by weight, or from about 0.3% to about 0.6% by weight of the detergent compositions disclosed herein.

Hygiene and malodour

The compositions of the present invention may also comprise one or more of zinc ricinoleate, thymol, quaternary ammonium salts such as Bardac®, polyethylenimines (such as Lupasol® from BASF) and zinc complexes thereof, silver and silver compounds, especially those designed to slowly release $Ag^+$ or nano-silver dispersions.

Probiotics

The compositions may comprise probiotics such as those described in WO2009/043709.

Fillers and Carriers

Fillers and carriers may be used in the cleaning compositions described herein. As used herein, the terms "filler" and "carrier" have the same meaning and can be used interchangeably.

Liquid cleaning compositions and other forms of cleaning compositions that include a liquid component (such as liquid-containing unit dose cleaning compositions) may contain water and other solvents as fillers or carriers. Suitable solvents also include lipophilic fluids, including siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, and mixtures thereof.

Low molecular weight primary or secondary alcohols exemplified by methanol, ethanol, propanol, and isopropanol are suitable. Monohydric alcohols may be used in some examples for solubilizing surfactants, and polyols such as those containing from 2 to about 6 carbon atoms and from 2 to about 6 hydroxy groups (e.g., 1,3-propanediol, ethylene glycol, glycerine, and 1,2-propanediol) may also be used. Amine-containing solvents, such as monoethanolamine, diethanolamine and triethanolamine, may also be used.

The cleaning compositions may contain from about 5% to about 90%, and in some examples, from about 10% to about 50%, by weight of the composition, of such carriers. For compact or super-compact heavy duty liquid or other forms of cleaning compositions, the use of water may be lower than about 40% by weight of the composition, or lower than about 20%, or lower than about 5%, or less than about 4% free water, or less than about 3% free water, or less than about 2% free water, or substantially free of free water (i.e., anhydrous).

For powder or bar cleaning compositions, or forms that include a solid or powder component (such as powder-containing unit dose cleaning composition), suitable fillers may include, but are not limited to, sodium sulfate, sodium chloride, clay, or other inert solid ingredients. Fillers may also include biomass or decolorized biomass. Fillers in granular, bar, or other solid cleaning compositions may comprise less than about 80% by weight of the cleaning composition, and in some examples, less than about 50% by weight of the cleaning composition. Compact or supercompact powder or solid cleaning compositions may comprise less than about 40% filler by weight of the cleaning composition, or less than about 20%, or less than about 10%.

For either compacted or supercompacted liquid or powder cleaning compositions, or other forms, the level of liquid or solid filler in the product may be reduced, such that either the same amount of active chemistry is delivered to the wash liquor as compared to noncompacted cleaning compositions, or in some examples, the cleaning composition is more efficient such that less active chemistry is delivered to the wash liquor as compared to noncompacted compositions. For example, the wash liquor may be formed by contacting the cleaning composition to water in such an amount so that the concentration of cleaning composition in the wash liquor is from above 0 g/l to 6 g/l. In some examples, the concentration may be from about 0.5 g/l to about 5 g/l, or to about 3.0 g/l, or to about 2.5 g/l, or to about 2.0 g/l, or to about 1.5 g/l, or from about 0 g/l to about 1.0 g/l, or from about 0 g/l to about 0.5 g/l. These dosages are not intended to be limiting, and other dosages may be used that will be apparent to those of ordinary skill in the art.

Buffer System

The cleaning compositions described herein may be formulated such that, during use in aqueous cleaning operations, the wash water will have a pH of between about 7.0 and about 12, and in some examples, between about 7.0 and about 11. Techniques for controlling pH at recommended usage levels include the use of buffers, alkalis, or acids, and are well known to those skilled in the art. These include, but are not limited to, the use of sodium carbonate, citric acid or sodium citrate, lactic acid or lactate, monoethanol amine or other amines, boric acid or borates, and other pH-adjusting compounds well known in the art.

The cleaning compositions herein may comprise dynamic in-wash pH profiles. Such cleaning compositions may use wax-covered citric acid particles in conjunction with other pH control agents such that (i) about 3 minutes after contact with water, the pH of the wash liquor is greater than 10; (ii) about 10 minutes after contact with water, the pH of the wash liquor is less than 9.5; (iii) about 20 minutes after contact with water, the pH of the wash liquor is less than 9.0; and (iv) optionally, wherein, the equilibrium pH of the wash liquor is in the range of from about 7.0 to about 8.5.

Test Methods

Partitioning Index Test Method

The Partitioning Index of an antifoam composition is determined using Nuclear Magnetic Resonance (NMR) analysis of a sample of a Model Detergent.

The Model Detergent composition is made by mixing together the formulation ingredients listed in the Model Detergent Ingredient Table—1 provided herein, in the order and proportions specified[1]. Once made, the Model Detergent composition is stored in a closed container for 3 days at 20-25° C. before samples are prepared and analyzed via NMR in accordance with the Partitioning Index Test Method specifications provided herein.

TABLE 1

| Model Detergent | |
|---|---|
| Model Detergent Ingredients[1] | Wt % |
| $C_{12}$-$C_{15}$ alkyl polyethoxylate (1.8) sulfate[2] | 8.55 |
| Sodium Hydroxide[3] | 0.21 |
| Ethanol[3] | 1.23 |
| 1,2-propylene glycol[3] | 1.74 |
| Diethylene glycol[3] | 1.22 |
| Diethylenetriamine pentaacetic acid[3] | 0.45 |
| Fluorescent Whitening Agent[4] | 0.064 |
| Monoethanolamine[3] | 1.22 |
| $C_{12}$-$C_{14}$ alkyl dimethyl amine oxide[5] | 0.53 |
| Sodium tetraborate[3] | 1.59 |
| $C_{11.8}$ linear alkylbenzne sulfonic acid[6] | 1.53 |
| Sodium formate[3] | 1.21 |
| Citric acid[3] | 2.24 |
| $C_{12}$-$C_{18}$ fatty acid[5] | 0.53 |
| Calcium formate[3] | 0.12 |
| Water; deionized | to 100% and pH = 8.0 to 8.2 |
| Protease[7] | 0.026 |
| Dye[8] | 0.015 |

TABLE 1-continued

| Model Detergent | |
|---|---|
| Model Detergent Ingredients[1] | Wt % |
| 2-hexenal[3] | 0.80 |
| Amylase[9] | 0.0038 |
| Antifoam composition to be tested | 0.10 |
| Trihydroxystearin[10] | 0.082 |

[1]An appropriately sized container is used to contain the mixture. Mixing is done using an overhead mixer equipped with a four-bladed propeller stirrer and 10 cm head diameter (such as the IKA model RW20D-S1 with R 1345 four-bladed propeller stirrer, as available from VWR Randor, Pennsylvania, VWR order catalog number 33994-112).
[2]Available from Shell Chemicals, Houston, TX.
[3]Available from Sigma-Aldrich Chemicals, Milwaukee, WI.
[4]Available from Ciba Specialty Chemicals, High Point, NC.
[5]Available from P&G Chemicals, Cincinnati, OH.
[6]Available from Huntsman Chemicals, Salt Lake City, UT.
[7]Available from DuPont Industrial Biosciences, South San Francisco, CA.
[8]Available from Milliken under the trade name Liquitint Green 101[9]
[9]Available from Novozymes, Copenhagen, Denmark under the tradename Everest 200L.
[10]Available under the tradename Thixin ® from Elementis Specialties, Highstown, NJ Two samples are taken from the Model Detergent containing the antifoam composition (which has been aged for 3 days at 20-25° C. after preparation). First sample is prepared by using a plastic pipette to place 5 drops (approximately 0.1 g) of the aged Model Detergent directly into a clean 50 mL round bottom flask (single-necked, 24/40, such as model Z414484 available from Sigma-Aldrich), and then following the dewatering and dissolution instructions provided further below. The second sample is prepared by centrifugation as according to the following instructions prior to undergoing the same dewatering and dissolution procedures specified. The centrifuged sample is prepared by using a disposable plastic pipette to transfer approximately 9 g of the aged Model Detergent with antifoam composition into a labeled centrifuge tube (such as a 10 mL volume, 16 mm×1 mm sized, polypropylene centrifuge tube with Screw-On Cap, as available model #364695 from Beckman Coulter Inc.). This sample is then centrifuged for 4 hours at approximately 30,000 g at 25° C. (such as at 15,300 revolutions per minute using a Beckman Coulter Allegra X-22R Centrifuge equipped with a Beckman F1010 Rotor). After centrifugation, approximately 0.5 mL of the sample is carefully removed from the center (middle level) of the material in the centrifuge tube. A disposable plastic pipette is used to obtain this sample in such a way that contamination from the upper and lower sections of the Model Detergent does not occur. Light pressure may be applied to the bulb of the pipette while inserting and removing the pipette into the sample, causing a few air bubbles to ensure no contamination is acquired from upper portion of the sample. The outer surface of the pipette is carefully wiped clean while still applying pressure to the bulb. Five drops of the centrifuged sample in the pipette are then disposed, and the following 5 drops of centrifuged sample (approximately 0.1 g) are carefully added to a clean 50 mL round bottom flask.

For each of the two samples obtained (i.e., the uncentrifuged sample and the centrifuged sample), dewatering is achieved by using a vacuum pump (such as model 1402N, Welch Chem Star) and adapter (such as 24/40 Vacuum adapter model Z137057, Sigma-Aldrich) to remove water from each sample while applying even heat to each flask for 30 seconds, such that a flask glass temperature of 60° C. is not exceeded. This heating step may employ a heat gun such as the Master Heat Gun Model HG-501A (Master Appliance Corp.). After the heat is removed, the sample is allowed to cool in the flask for 6 min under the reduced pressure provided by the vacuum pump. The pressure is equalized and the adapter removed. For each of the two dewatered samples, a glass pipette is used to add about 1 mL of chloroform-d (such as Chloroform-D, 99.8 ATOM % D, available from Sigma-Aldrich catalogue number 151823) into each flask, to separately dissolved each sample. For each sample, after maximum sample solvation in chloroform is achieved then 0.75 mL of the prepared sample is placed into a clean and labeled NMR tube and sealed with a cap. Suitable NMR tubes include the model Z569267 Colorspec NMR Tubes and caps (Sigma-Aldrich).

Quantitative $^1$H NMR data is acquired for each prepared sample using an NMR spectrometer equipped with a 5 mm PABBO Z-GRD probe, such as instrument model Avance III HD 400 MHz (Bruker Corp., Billerica, Mass., USA), or equivalent. The instrument is set up with the parameters listed as follows: 30 degree pulse; 1 second recycle delay; 256 scans; PROBHD—5 mm PABBO BB/; PULPROG—zg30; TD—65536; Solvent—CDCl3; DS—2; SWH—8012.820 Hz; FIDRES—0.122266 Hz; AQ—4.0894465 seconds; RG—96.94; DW—62.400 microseconds; DE—17.73 microseconds; TE—297.3 Kelvin; D1—1.0 seconds; TDO—1; SFO1—400.1324710 MHz; NUC1—1H; P1—10.00 microseconds; PLW1—14.21000004 W; SI—65536; SF400.130 MHz; WDW—EM; SSB—0; LB—0.30 Hz; GB—0; PC—1.00. For each of the two samples (i.e.,centrifuged and uncentrifuged), the acquired data are analyzed by setting the CDCl$_3$ chemical shift to 7.24 ppm. Software such as the MestReNova LITE Version 5.2.5-5780 (Mestrelab Research S.L.) is used to quantitatively integrate a unique chemical shift of the organomodified silicone, and to quantitatively integrate the unique chemical shift of the aromatic proton from 7.60 to 7.85 ppm. One example of a suitable unique shift in a specific given siloxane is the methyl group of the 2-phenylpropylmethylsiloxane repeat unit at −0.20 to −0.09 ppm. The chemical shift of the aromatic proton at 7.60 to 7.85 ppm is normalized to a value of 20, and the resultant normalized integral value of the organomodified silicone chemical shift is recorded.

The Partitioning Index of the antifoam composition is calculated using the following formula $$\text{The Partitioning Index of the antifoam composition} = 100 \times \left(\frac{\text{Centrifuged Sample}}{\text{Uncentrifuged Sample}}\right)$$

wherein Centrifuged Test sample=The normalized integral value of the organomodified silicone chemical shift in centrifuged sample, and Uncentrifuged sample=The normalized integral value of the organomodified silicone chemical shift in the uncentrifuged sample.

An example of the Partitioning Index calculation for a given antifoam composition A is provided as follows: For a given antifoam composition A, formulated into the Model Detergent as specified for the purpose of testing, the control sample is the Uncentrifuged formulation of the antifoam composition in the Model Detergent (Uncentrifuged sample), and the test sample is the Centrifuged sample of the antifoam composition in the Model Detergent (Centrifuged sample). Where the normalized integral values calculated from the NMR measurements are as given below:

normalized integral value of the organomodified silicone in the Uncentrifuged sample=1.35 normalized integral value of the organomodified silicone in the Centrifuged sample=0.65, then the Partitioning Index of the given test antifoam composition A=((0.65/1.35))×100=48.

Methanol Absorption Index Test Method

Silica surfaces that have been modified with non-hydrolysable organic molecules (i.e., made more hydrophobic) may be poorly wetted by water; however such hydrophobic silicas may become wetted after exposure to aqueous methanol. Silica is classified herein as either Wetted or Non-Wetted, according to its sedimentation behavior in aqueous methanol. Silica that forms sediment in aqueous methanol after centrifugation under specified conditions is defined as Wetted silica, while the non-sedimenting silica is defined as being Non-wetted. The volume of silica that is wetted upon exposure to a given concentration of aqueous methanol is a measure of the hydrophobicity of the modified silica, and is used herein to determine the Methanol Absorption Index of the silica.

Two aqueous methanol solutions are prepared using deionized water (DI), to yield a 54% (wt/wt) methanol solution, and also a 90% (wt/wt) methanol solution. The 90% methanol solution serves as a positive control reference point which achieves maximum wetting of the silica. Prior to testing, the silica is preconditioned by allowing it to equilibrate with atmospheric conditions within the range of 21° C. to 25° C. in temperature, and within the relative humidity range of 20% RH to 50% RH. The conditioned silica is mixed thoroughly and allowed to settle for several minutes, to ensure homogeneity before sampling. Sampling of the silica results in paired aliquots of silica, wherein one pair comprises one replicate. At least two replicate pairs of aliquots are prepared from each silica being tested. For each replicate pair, two aliquots of the silica are weighed out, wherein each aliquot in the pair comprises 200 mg +/−1 mg of silica which is placed into a centrifuge tube. The centrifuge tubes are 15 mL capacity transparent plastic tubes with screw top lids and a graduated volumetric scale, wherein the scale has graduations of 0.5 mL and 0.1 mL for at least the first 1 mL of volume. Suitable tubes include the model # 21008-197 available from VWR International LLC, Radnor, Pa., USA. Methanol solution is added to both tubes in each replicate pair of tubes. One tube in each pair receives 8 mL of the 54% methanol solution, while the other tube in the pair receives 8 mL of the 90% methanol solution. Each tube containing silica sample and methanol solution is then sealed with a lid.

Each sealed sample tube is vigorously shaken by hand ten times in a vertical up and down motion, and is then immediately vortexed for 45 seconds on a benchtop vortex mixer (such as Mini-vortexer model #58816-121 from VWR International LLC, Radnor, Pa., USA) using the maximum speed setting. After shaking and vortexing, the mixing process is repeated such that each sample tube is shaken and vortexed twice. Immediately after the mixing is complete each tube is placed into a centrifuge and centrifuged at an average relative centrifugal force (RCF) of 851 g for 5 minutes, at 25° C. One instrument suitable for this process is the model Allegra X-22R Centrifuge equipped with SX4250 Rotor and adapter #392253 run at 2500 RPM (as available from Beckman Coulter Inc., Brea, Calif., USA).

Immediately after the centrifugation is complete, the volume of sediment in each centrifuged sample tube is determined by reading the graduated scale markings on the tube, with an accuracy of 0.05 mL. For each silica, the measured volumes obtained from at least two replicates of paired samples are used to separately calculate the average sediment volume for each of the two methanol concentrations. For each silica, the ratio is then calculated using the average sediment volumes that were obtained from the two different methanol concentrations, wherein the average result from the lower methanol concentration (i.e., 54%) is divided by the average result from the higher methanol concentration (i.e., 90%). This ratio of the sediment volumes is then multiplied by 100, to yield the Methanol Absorption Index value of that silica, which is the reported value. These calculations are conducted for each silica in accordance with the equation below:

Methanol Absorption Index=(Sediment in low/Sediment in high)×100 wherein:

Sediment in low=the average volume of sediment (in mL) in 54% methanol, and Sediment in high=the average volume of sediment (in mL) in 90% methanol.

Antifoam Performance Test Method

The liquid detergent containing the antifoam composition was tested using the Antifoam Performance Test within 24 hours of making the detergent. The composition is then stored in a controlled temperature and humidity at 32.2° C. and 80% relative humidity. After 1, 2 and 3 months of storage the composition is retested for the antifoam performance.

The fabric load used in the Antifoam Performance Test consists of six 100% cotton T-shirts, six 50/50 polyester/cotton blend pillowcases, and six 86/14 polyester/cotton blend towels, totaling 8-8.5 lb. A clean, dry fabric load must be used for each test replicate. If the fabric load is reused, it is thoroughly cleaned in a Kenmore 600 series washing machine or equivalent using the heavy duty or cotton/sturdy setting, hot water at 60° C. (±3° C.), and 90.72 g of liquid Tide® Free or equivalent. The washing is repeated two times. The fabric load is washed third, fourth and fifth time after the conclusion of the previously described second cycle with the exception that no detergent is added during the third, fourth, and fifth cycles. During the fifth cycle, there should be no suds visible in the washing machine during the wash or rinse portions of the wash cycle. If suds are present, additional cycles, with the same wash cycle parameters as described above for the first wash cycle, are ran with the exception that no detergent is added to these additional cycles. These additional cycles continue to be repeated until no suds are present during the wash and rinse cycles. Once no suds are observed in the wash or rinse portions of the wash cycle, the fabric load is removed from the washing machine and dried in an electric dryer on the high heat setting for approximately 55 minutes or until the fabric load is completely dry.

A dose of 46.55 g of the liquid detergent to be tested is weighed in plastic cups. A Whrilpool® Duet front loading washing machine, model number GHW9100, or equivalent is used for measuring the antifoam performance in the Antifoam Performance Test. The length of each wash cycle is measured with a digital timer. The washing machines are cleaned prior to use by running them through a wash cycle, empty (without fabric load or detergent) with soft water at 49° C. (±1°. This cycle is repeated until no suds are observed during the cycle. This cleaning procedure is conducted between each cycle in which a detergent product with antifoam is tested.

Once the washing machine is cleaned, the fabric load is then placed to the washing machine. The pre-weighed detergent in the plastic cup described above is emptied into the washer dosing drawer. The plastic cup in which the sample was weighed is placed into the back of the drum of the washer. The Antifoam Performance Test is ran using a normal wash cycle with soft water (zero grains/gal hardness) at a temperature of 37° C. (±3° during the wash cycle and 21° C. (±3° rinse cycle. The hardness and temperature of the water are monitored throughout the duration of the test. The washing machine should not be paused at any time during the test.

The suds height data and the state of the washing machine, such as spinning, filling, tumbling, draining, and suds lock, are recorded every 2 minutes. The suds height is measured by assigning a score of 0 to 4 every two minutes, with 0 indicating no suds are present, 1 indicating suds are present among the clothes, 2 indicating suds are one-third of the way up the window, 3 indicating suds are two-thirds of the way up the window, and 4 indicating the suds are covering the window completely. At the end of the cycle, the digital timer on the washing machine must be stopped within 5 seconds of the washing machine stopping. The time displayed on the digital timer is recorded as the actual total cycle time. The test is repeated three times for each test product and the cycle time results are averaged to determine the performance of the antifoam.

The sample is designated to have a "Pass" grade if all of the following criteria are met. It is designated to have a "Fail' grade if any one of the criteria are not met:

a. the cycle time is less than or equal to 65 minutes
b. a suds height of 2.0 or below is observed throughout the duration of the cycle, and
c. suds locks or suds lock errors are not displayed on the machine, on at least two of the three replicates during the test If the detergent is designated to have a "Fail" grade at fresh, one month, or two months, testing is not done for the subsequent storage time intervals.

Viscosity Test Method

A preliminary estimate of the sample viscosity at 25° C. and $6.325s^{-1}$ is used to select the appropriate instrument geometry to be used during the final viscosity measurement analyses, which are conducted on a model AR-G2 Rheometer (manufactured by TA Instruments Corp., New Castle, Del., USA). A preliminary estimate of the sample viscosity may be obtained by using a Brookfield Viscometer (Brookfield Engineering Laboratories Inc., Middleboro, Mass., USA). The selection of geometry for use on the AR-G2 Rheometer is determined in accordance with the following table, Table-2:

TABLE 2

| AR-G2 Geometry Selection | |
|---|---|
| Preliminary Estimate of Sample Viscosity | AR-G2 Geometry and Plate Size |
| >1000 Pa*s | 25 mm parallel plate |
| 1 to 1000 Pa*s | 40 mm parallel plate |
| >Water-thin to <1 Pa*s | 60 mm parallel plate |
| Water-thin | Couette/Cup and Bob |

The geometry attached to the instrument, the instrument is mapped, the gap distance is zeroed, and the instrument temperature is set to 25° C. The measurement mode is selected as Stiff Mode when using parallel plates, or to Soft mode when using the couett cup and bob geometry. Sample material is mounted into the sample holding geometry e.g., the base plate. The minimum gap distance allowable between the base plate and the selected geometry is 10× the diameter of the largest common particle present in sample. If there are common particles in the sample which have a diameter greater than 100 µm (as determined microscopically), then the gap value is set to 10× the diameter of the largest common particle, otherwise the gap distance is set to the default value of 1000 µm (ie 1 mm). The selected geometry is lowered to the appropriate gap and a plastic tool is used to trim off any excess sample material. The sample material is allowed to equilibrate to the temperature of the instrument. Three rheological measurement analyses are conducted, namely: Flow Curve, Stress Sweep, and Frequency Sweep, using the following selections and settings:

Flow Curve: select Stepped Flow 0.01 to 100; 10 pts/decade; shear stress; constant time 20; average last 10.

Stress Sweep: set the Stress Range as 0.01 to 100 Pa; set the Frequency at 1 rad/s.

Frequency Sweep: Set the Angular Frequency Range as 0.1 to 100.

To ensure that the analysis is conducted within the Linear Viscoelastic Region set the Stress value at a third of the stress value that was present when G' started to degrade during the prior Stress Sweep analysis.

The viscosity value for the test material obtained at $6.325s^{-1}$ at 25° C. is reported as the viscosity value of the sample in cSt, ±300cSt.

LogP Method for Non-cyclic Aliphatic Moiety/Material

In order to conduct the calculations involved in the computed-value test methods described herein, the starting information required includes the identity, weight percent, and molar percent of each non-cyclic aliphatic moiety being tested, as a proportion of that mixture, wherein all non-cyclic aliphatic moiety in the mixture composition are included in the calculations. Additionally for each of those non-cyclic aliphatic moiety, the molecular structure, and the values of various computationally-derived molecular descriptors are also required, as determined in accordance with the Test Method for the Generation of Molecular Descriptors described herein.

Test Method for Determining the Logarithm of the Octanol/Water Partition Coefficient (logP)

The value of the log of the Octanol/Water Partition Coefficient (logP) is computed for each non-cyclic aliphatic moiety in the mixture composition being tested. The logP of an individual non-cyclic aliphatic moiety is calculated using the Consensus logP Computational Model, version 14.02 (Linux) available from Advanced Chemistry Development Inc. (ACD/Labs) (Toronto, Canada) to provide the unitless logP value. The ACD/Labs' Consensus logP Computational Model is part of the ACD/Labs model suite.

Test Method for the Generation of Molecular Descriptors

For each non-cyclic aliphatic moiety in a mixture composition its molecular structure is used to compute various molecular descriptors. The molecular structure is determined by the graphic molecular structure representations provided by the Chemical Abstract Service ("CAS"), a division of the American Chemical Society, Columbus, Ohio, U.S.A. These molecular structures may be obtained from the CAS Chemical Registry System database by looking up the index name or CAS number of each non-cyclic aliphatic moiety. For non-cyclic aliphatic moieties, which at the time of their testing are not yet listed in the CAS Chemical Registry System database, other databases or information sources may be used to determine their structures. For a non-cyclic aliphatic moiety which has potentially more than one isomer present, the molecular descriptor computations are conducted using the molecular structure of only one of the isomers, which is selected to represent that non-cyclic aliphatic moiety. The selection of isomer is determined by the relative amount of extension in the molecular structures of the isomers. Of all the isomers of a given non-cyclic aliphatic moiety, it is the isomer whose molecular structure is the most prevalent by weight % which is the one that is selected to represent that non-cyclic aliphatic moiety. The structures for other potential isomers of that non-cyclic aliphatic moiety are excluded from the computations. The molecular structure of the most prevalent isomer is paired with the concentration of that non-cyclic aliphatic moiety, where the concentration reflects the presence of all the isomers of that non-cyclic aliphatic moiety that are present.

A molecule editor or molecular sketching software program, such as ChemDraw (CambridgeSoft/PerkinElmer Inc., Waltham, Mass., U.S.A.), is used to duplicate the 2-dimensional molecular structure representing each non-cyclic aliphatic moiety. Molecular structures should be represented as neutral species (quaternary nitrogen atoms are allowed) with no disconnected fragments (e.g., single structures with no counter ions). The winMolconn program described below can convert any deprotonated functional groups to the neutral form by adding the appropriate number of hydrogen atoms and will discard the counter ion.

For each non-cyclic aliphatic moiety, the molecular sketching software is used to generate a file which describes the molecular structure of the non-cyclic aliphatic moiety. The file(s) describing the molecular structures of the non-cyclic aliphatic moieties is subsequently submitted to the computer software program winMolconn, version 1.0.1.3 (Hall Associates Consulting, Quincy, Mass., U.S.A., www-.molconn.com), in order to derive various molecular descriptors for each non-cyclic aliphatic moiety. As such, it is the winMolconn software program which dictates the structure notations and file formats that are acceptable options. These options include either a MACCS SDF formatted file (i.e., a Structure-Data File); or a Simplified Molecular Input Line Entry Specification (i.e., a SMILES string structure line notation) which is commonly used within a simple text file, often with a ".smi" or ".txt" file name extension. The SDF file represents each molecular structure in the format of a multi-line record, while the syntax for a SMILES structure is a single line of text with no white space. A structure name or identifier can be added to the SMILES string by including it on the same line following the SMILES string and separated by a space, e.g.: C1=CC=CC=C1 benzene.

The winMolconn software program is used to generate numerous molecular descriptors for each non-cyclic aliphatic moiety, which are then output in a table format. Specific molecular descriptors derived by winMolconn are subsequently used as inputs (i.e., as variable terms in mathematical equations) for a variety of computer model test methods in order to calculate values such as: logarithm of the Octanol/Water Partition Coefficient (logP). The molecular descriptor labels used in the models' test method computations are the same labels reported by the winMolconn program, and their descriptions and definitions can be found listed in the winMolconn documentation. The following is a generic description of how to execute the winMolconn software program and generate the required molecular structure descriptors for each non-cyclic aliphatic moiety in a composition.

Computing Molecular Structure Descriptors using winMolconn:
1) Assemble the molecular structure for one or more perfume ingredients in the form of a MACCS Structure-Data File, also called an SDF file, or as a SMILES file.
2) Using version 1.0.1.3 of the winMolconn program, running on an appropriate computer, compute the full complement of molecular descriptors that are available from the program, using the SDF or SMILES file described above as input.
   a. The output of winMolconn is in the form of an ASCII text file, typically space delimited, containing the structure identifiers in the first column and respective molecular descriptors in the remaining columns for each structure in the input file.
3) Parse the text file into columns using a spreadsheet software program or some other appropriate technique. The molecular descriptor labels are found on the first row of the resulting table.
4) Find and extract the descriptor columns, identified by the molecular descriptor label, corresponding to the inputs required for each model.
   a. Note that the winMolconn molecular descriptor labels are case-sensitive.

Test Method for Silica Particle Size

Silica particle size (d50) is determined by ISO method, ISO 13320-2009

EXAMPLES

Example 1

The antifoam molecule is prepared by mixing 22.75 g of an organomodified silicone, APT-213[11], having a viscosity of approximately 1200-1600 cSt. and comprising 75-85 mole % ethylmethylsiloxane groups, 15-25 mole % 2-phenylpropylmethylsiloxane groups and terminated with a trimethylsilyl group, 0.99 g of an organosiloxane resin, Wacker-Belsil TMS 803 MQ[12], having trimethyl siloxane units and $SiO_2$ units in a M/Q ratio of about 0.65/1 to 0.67/1, 1.24 g of precipitated silica, Sipernat D10[13], and 0.20 g of potassium methoxide[3], for 4 hr at 190° C. The resultant product is an antifoam material. The resultant product is cooled to ambient, filtered, washed thoroughly with methanol and dried to isolate the antifoam molecule.

Example 2

A control molecule for use as a negative example is prepared by mixing together 22.75 g of an organomodified silicone, APT-213[11], having a viscosity of approximately 1200-1600 cSt. and comprising 75-85 mole % ethylmethylsiloxane groups, 15-25 mole % 2-phenylpropylmethylsiloxane groups and terminated with a trimethylsilyi group, 1.00 g of an organosiloxane resin, Wacker-Belsil TMS 803 MQ[12], having trimethyl siloxane units and $SiO_2$ units in a M/Q ratio of about 0.65/1 to 0.67/1 and 1.25 g of precipitated silica, Sipernat D10[13]. The resultant product is a negative antifoam control material for use as a negative example. The resultant product can be filtered, washed thoroughly with methanol, and dried to yield the control molecule.

Example 3

The antifoam molecule is prepared by mixing 22.75 g of an organomodified silicone, APT-213[11], having a viscosity of approximately 12004600 cSt. and comprising 75-85 mole % ethylmethylsiloxane groups, 15-25 mole % 2-phenylpropyhnethylsiloxane groups and terminated with a trimethylsilyl group, 1.00 g of an organosiloxane resin, Wacker-Belsil TMS 803 MQ[12], having trimethyl siloxane units and $SiO_2$ units in a M/Q ratio of about 0.65/1 to 0.67/1, 1.25 g of precipitated silica, Sipernat D35[13], and 0.20 g of potassium methoxide[3], for 4 hr at 190° C. The resultant product is an antifoam material. The resultant product is cooled to ambient, filtered, washed thoroughly with methanol, and dried to isolate the antifoam molecule.

Example 4

A control for use as a negative example is prepared by mixing together 22.75 g of an organomodified silicone. APT-213[11], having a viscosity of approximately 1200-1600 cSt. and comprising 75-85 mole % ethylmethylsiloxane groups, 15-25 mole % 2-phenylpropylmethylsiloxane groups and terminated with a trimethylsilyl group, 1.00 g of an organosiloxane resin, Wacker-Belsil TMS 803 MQ[12] having trimethyl siloxane units and $SiO_2$ units in a NW ratio of about 0.65/1 to 0.67/1 and 1.25 g of precipitated silica, Sipernat D35[13]. The resultant product is a negative antifoam control material for use as a negative example. The resultant product can be filtered, washed thoroughly with methanol and dried to yield the control molecule.

Example 5

The antifoam molecule is prepared by mixing 40 g of an organomodified silicone, PDS-1615[11], having a viscosity of approximately 50-60 cSt. and comprising 82-86 mole % dimethyisilsiloxane groups, 14-18 mole % 2-phenylpropylmethylsiloxane groups and terminated with a silanol group, 0.86 g of an organosiloxane resin, Wacker-Belsil TMS 803 MQ[12], having trimethyl siloxane units and $SiO_2$ units in a M/Q ratio of about 0.65/1 to 0.67/1, 1.61 g of precipitated silica, Sipernat D10[13], 0.54 g of fumed silica, Aerosil R972[13] and 0.20 g of potassium methoxide[3], for 4 hr at 150° C. The resultant product is an antifoam material. The resultant product is cooled to ambient, filtered, washed thoroughly with methanol, and dried to isolate the antifoam molecule.

Example 6

A control molecule is prepared by mixing together 23.25 g of an organomodified silicone, DS-1615[11], having a viscosity of approximately 50-60 cSt. and comprising 82-86 mole % dimethylsiloxane groups, 14-18 mole % 2-phenylpropylmethylsiloxane groups and terminated with a silanol group, 0.5 g of an organosiloxane resin, Wacker-Belsil TMS 803 MQ[12], having trimethyl siloxane units and $SiO_2$ units in a M/Q ratio of about 0.65/1.to 0.67/1, 0.94 g of precipitated silica, Sipernat D10[13] and 0.31 g of fumed silica, Aerosil R972[13]. The resultant product is a negative antifoam control material for use as a negative example. The resultant product can be filtered, washed thoroughly with methanol, and dried to yield the control molecule.

Example 7

The antifoam molecule is prepared by mixing 22.75 g of an organomodified silicone, APT-213[11], having a viscosity of approximately 1200-1600 cSt. and comprising 75-85 mole % ethylmethylsiloxane groups, 15-25 mole % 2-phenylpropylmethylsiloxane groups and terminated with a trimethylsilyl group, 7.60 g of an organosiloxane resin, Wacker-Belsil TMS 803 MQ[12], having trimethyl siloxane units and $SiO_2$ units in a M/Q ratio of about 0.65/1 to 0.67/1, 10.00 g of precipitated silica, Sipernat D10[13], and 0.20 g of potassium methoxide[3], for 2 hr at 190° C. Half of the resultant material is cooled to ambient, filtered, washed thoroughly with methanol, and dried to isolate the antifoam molecule. Half of the resultant material is cooled to ambient and 17.64 g of 10 cSt. polydimethlysiloxane[11] and 3.00 g of 2-ethylhexyl stearate[14] is added and completely incorporated by mixing to yield the antifoam material.

Example 8

The antifoam molecule is prepared by mixing 42.34 g of an organomodified silicone, AFT-213[11]. having a viscosity of approximately 1200-1600 cSt. and comprising 75-85 mole % ethylmethylsiloxane groups, 15-25 mole % 2-phenylpropylmethylsiloxane groups and terminated with a trimethylsilyl group, 2.28 g of an organosiloxane resin, Wacker-Belsil TMS 803 MQ[12], having trimethyl siloxane units and $SiO_2$ units in a M/Q ratio of about 0.65/1 to 0.67/1, 3.00 g of precipitated silica, Sipernat 35[13], and 0.06 g of potassium methoxide[3], for 2 hr at 190° C. Half of the resultant material is cooled to ambient, filtered, washed thoroughly with methanol, and dried to isolate the antifoam molecule. Half of the resultant product is cooled to ambient and 5.29 g of 10 cSt. polydimethlysiloxane[11] and 0.9 g of 2-ethylhexyl stearate[14] is added and completely incorporated by mixing to yield the antifoam material.

Example 9

The antifoam molecule is prepared by mixing 42.34 g of an organomodified silicone, PDS-0338[11], having a viscosity of approximately 6000-8000 cSt. and comprising 96.5-97.5 mole % dimethylsiloxane groups, 2.5-3.5 mole % diphenylsiloxane groups and terminated with a silanol group, 2.2.8 g of an organosiloxane resin, Wacker-Belsil TMS 803 MQ[12], having trimethyl siloxane units and $SiO_2$ units in a M/Q ratio of about 0.65/1 to 0.67/1, 3.00 g of precipitated silica, Sipernat 35[13], and 0.06 g of potassium methoxide[3], for 2 hr at 190° C. Half of the resultant material is cooled to ambient, filtered, washed thoroughly with methanol, and dried to isolate the antifoam molecule. Half of the resultant product is cooled to ambient and 5.29 g of 10 cSt. polydimethlysiloxane and 0.9 g of 2-ethylhexyl stearate[14] is added and completely incorporated by mixing to yield the antifoam material.

Example 10

The antifoam molecule is prepared by mixing 42.34 g of an organomodified silicone, PDV-0535[11], having a viscosity of approximately 5000 cSt. and comprising 94-96 mole % dimethylsiloxane groups, 4-6 mole % diphenyisiloxane groups and terminated with a vinyl group, 2.28 g of an organosiloxane resin, Wacker-Belsil TMS 803 MQ[12], having trimethyl siloxane units and $SiO_2$ units in a M/Q ratio of about 0.65/1 to 0.67/1, 3.00 g of precipitated silica, Sipernat 35[13], and 0.06 g of potassium methoxide[3], for 2 hr at 190° C. Half of the resultant material is cooled to ambient, filtered, washed thoroughly with methanol, and dried to isolate the antifoam molecule. Half of the resultant product is cooled to ambient and 5.29 g of 10 cSt. polydimethlysiloxane[11] and 0.9 g of 2-ethylhexyl stearate[14] is added and completely incorporated by mixing to yield the antifoam material.

Example 11

The antifoam molecule is prepared by mixing 141.12 g of an organomodified silicone, APT-213[11], having a viscosity of approximately 1200-1600 cSt. and comprising 75-85 mole % ethylmethylsiloxane groups, 15-25 mole % 2-phenylpropylmethylsiloxane groups and terminated with a trimethylsilyl group, 7.60 g of an organosiloxane resin, Wacker-Belsil TMS 803 MQ[12], having trimethyl siloxane units and $SiO_2$ units in a M/Q ratio of about 0.65/1 to 0.67/1, 10.00 g of precipitated silica, Sipernat D13[13], and 0.20 g of potassium methoxide[3], for 2 hr at 190° C. Half of the resultant material is cooled to ambient, filtered, washed thoroughly with methanol, and dried to isolate the antifoam molecule. Half of the resultant material is cooled to ambient and 17.64 g of 10 cSt. polydimethlysiloxane[1] and 3.00 g of 2-ethylhexyl stearate[11] is added and completely incorporated by mixing to yield the antifoam material.

Example 12

The antifoam molecule is prepared by mixing 141.12 g of an organomodified silicone, APT-213[11], having a viscosity of approximately 1200-1600 cSt. and comprising 75-85 mole % ethylmethylsiloxane groups, 15-25 mole % 2-phenylpropylmethylsiloxane groups and terminated with a trimethylsilyl group, 7.60 g of an organosiloxane resin, Wacker-Belsil TMS 803 MQ[12], having trimethyl siloxane units and $SiO_2$ units in a M/Q ratio of about 0.65/1 to 0.67/1, 10.00 g of precipitated silica, Sipernat 383 DS[13], and 0.20 g of potassium methoxide[3], for 2 hr at 190° C. Half of the resultant material is cooled to ambient, filtered, washed thoroughly with methanol, and dried to isolate the antifoam molecule. Half of the resultant material is cooled to ambient and 17.64 g of 10 cSt. polydimethlysiloxane[1] and 3.00 g of 2-ethylhexyl stearate[14] is added and completely incorporated by mixing to yield the antifoam material.

Example 13

The antifoam molecule is prepared by mixing 42.34 g of an organomodified silicone, APT-213[11], having a viscosity of approximately 1200-1600 cSt. and comprising 75-85 mole % ethylmethylsiloxane groups, 15-25 mole % 2-phenylpropylmethylsiloxane groups and terminated with a trimethylsityl group, 2.28 g of an organosiloxane resin, Wacker-Belsil TMS 803 MQ[12], having trimethyl siloxane units and $SiO_2$ units in a M/Q ratio of about 0.65/1 to 0.67/1, 1.95 g of precipitated silica, Sipernat 35[13], 1.05 g of fumed silica, Aerosil R972[13], and 0.06 g of potassium methoxide[3], for 2 hr at 190° C. Half of the resultant material is cooled to ambient, filtered, washed thoroughly with methanol, and dried to isolate the antifoam molecule. Half of the resultant product is cooled to ambient and 5.29 g of 10 cSt. polydimethlysiloxane[11] and 0.9 g of 2-ethylhexyl stearate[14] is added and completely incorporated by mixing to yield the antifoam material.

Example 14

The antifoam molecule is prepared by mixing 42.34 g of an organomodified silicone, PMM-6025[11], having a viscosity of approximately 500 cSt. and comprising 38-42 mole % dimethylsiloxane groups, 58-62 mole % phenylmethylsiloxane groups and terminated with a vinyl group, 2.28 g of an organosiloxane resin, Wacker-Belsil TMS 803 MQ[11], having trimethyl siloxane units and $SiO_2$ units in a M/Q ratio of about 0.65/1 to 0.67/1, 3.00 g of precipitated silica, Sipernat 35[13], and 0.06 g of potassium methoxide[3], for 2 hr at 190° C. Half of the resultant material is cooled to ambient, filtered, washed thoroughly with methanol, and dried to isolate the antifoam molecule. Half of the resultant product is cooled to ambient and 5.29 g of 10 cSt. polydimethlysiloxane[11] and 0.9 g of 2-ethylhexyl stearate[14] is added and completely incorporated by mixing to yield the antifoam material.

Example 15A-15N

Liquid Detergent Composition

Liquid detergent fabric care composition for the formula was made by mixing together the ingredients listed in the order and proportions shown in Table-3 provided herein[1]:

TABLE 3

| Liquid detergent composition | |
|---|---|
| Liquid Detergent Composition Ingredients | Wt % |
| $C_{12}$-$C_{15}$ alkyl polyethoxylate (1.8) sulfate[2] | 8.55 |
| Sodium Hydroxide[3] | 0.21 |
| Ethanol[3] | 1.23 |
| 1,2-propylene glycol[3] | 1.74 |
| Diethylene glycol[3] | 1.22 |
| Diethylenetriamine pentaacetic acid[3] | 0.45 |
| Fluorescent Whitening Agent[4] | 0.064 |
| Monoethanolamine[3] | 1.22 |
| $C_{12}$-$C_{14}$ alkyl dimethyl amine oxide[5] | 0.53 |
| Sodium tetraborate[3] | 1.59 |
| $C_{11.8}$ linear alkylbenzne sulfonic acid[6] | 1.53 |
| Sodium formate[3] | 1.21 |
| Citric acid[3] | 2.24 |
| $C_{12}$-$C_{18}$ fatty acid[5] | 0.53 |
| Calcium formate[3] | 0.12 |
| Aromatic Perfume[15] | 0.066 |
| Non-aromatic perfume[16] | 0.48 |
| Perfume microcapsule[17] | 0.33 |
| Water, dyes, buffers, enzymes, solvents, and other optional components | to 100% pH 8.0 to 8.2 |
| Antifoam material of any of examples 1-14 prior to isolation of the antifoam molecule | 0.10 |
| Trihydroxylstearin[10] | 0.082 |

[3]Available from Sigma-Aldrich, Milwaukee, WI
[11]Available from Gelest, Inc., Morrisville, PA
[12]Supplied by Wacker Silicones, Adrian, MI
[13]Available from Evonik Degussa Corporation, Parsippany, NJ
[14]Supplied by Wako Chemicals USA, Inc, Richmond, VA
[1]An appropriately sized container is used to contain the mixture. Mixing is done using an IKA RW 20D S1 overhead mixer, model RW20D-S1 and a R 1345 four-bladed propeller stirrer, 10 cm head diameter, from VWR Randor, Pennsylvania, VWR order catalog number 33994-112.
[2]Available from Shell Chemicals, Houston, TX.
[3]Available from Sigma-Aldrich Chemicals, Milwaukee, WI.
[4]Available from Ciba Specialty Chemicals, High Point, NC.
[5]Available from P&G Chemicals, Cincinnati, OH.
[6]Available from Huntsman Chemicals, Salt Lake City, UT.
[10]Available under the tradename Thixin ® from Elementis Specialties, Highstown, NJ
[15]Perfume consisting of benzyl acetate, beta naphthol methyl ether, ethyl vanillin, eugenol, hexyl cinnamic aldehyde, methyl benzoate, methyl beta-naphthyl ketone, methyl phenyl carbonyl acetate
[16]Perfume consisting of aliphatic materials
[17]Available from Encapsys Inc, Appleton, WI Examples 1.6A-16E Liquid Detergent Composition Liquid detergent composition 16A-16E are made by mixing together the ingredients listed in the order and proportions shown[1] in Table-4:

TABLE 4

| Liquid Detergent Composition examples 16A-16E | | | | | |
|---|---|---|---|---|---|
| Ingredient (wt %) | 16A | 16B | 16C | 16D | 16E |
| $C_{12}$-$C_{15}$ alkyl polyethoxylate (1.8) sulfate[2] | 20.1 | 16.6 | 14.7 | 13.9 | 8.2 |
| $C_{11.8}$ linear alkylbenzene sulfonc acid[6] | — | 4.9 | 4.3 | 4.1 | 8.2 |
| $C_{16}$-$C_{17}$ branched alkyl sulfate[2] | — | 2.0 | 1.8 | 1.6 | — |
| $C_{12}$ alkyl trimethyl ammonium chloride[18] | 2.0 | — | — | — | — |
| $C_{12}$ alkyl dimethyl amine oxide[5] | — | 0.7 | 0.6 | — | — |
| $C_{12}$-$C_{14}$ alcohol 9 ethoxylate[19] | 0.3 | 0.8 | 0.9 | 0.6 | 0.7 |
| $C_{15}$-$C_{16}$ branched alcohol -7 ethoxylate[2] | — | — | — | — | 4.6 |
| 1,2 Propane diol[3] | 4.5 | 4.0 | 3.9 | 3.1 | 2.3 |
| Ethanol[3] | 3.4 | 2.3 | 2.0 | 1.9 | 1.2 |
| $C_{12}$-$C_{18}$ Fatty Acid[5] | 2.1 | 1.7 | 1.5 | 1.4 | 3.2 |
| Citric acid[20] | 3.4 | 3.2 | 3.5 | 2.7 | 3.9 |
| Protease[7] (32 g/L) | 0.42 | 1.3 | 0.07 | 0.5 | 1.12 |
| Fluorescent Whitening Agent[4] | 0.08 | 0.2 | 0.2 | 0.17 | 0.18 |
| Diethylenetriamine pentaacetic acid[3] | 0.5 | 0.3 | 0.3 | 0.3 | 0.2 |

TABLE 4-continued

| Liquid Detergent Composition examples 16A-16E | | | | | |
|---|---|---|---|---|---|
| Ingredient (wt %) | 16A | 16B | 16C | 16D | 16E |
| Ethoxylated polyamine[21] | 0.7 | 1.8 | 1.5 | 2.0 | 1.9 |
| Grease Cleaning Alkoxylated Polyalkylenimine Polymer[22] | — | — | 1.3 | 1.8 | — |
| Zwitterionic ethoxylated quaternized sulfated hexamethylene diamine[23] | — | 1.5 | — | — | 0.8 |
| Hydrogenated castor oil[10] | 0.2 | 0.2 | | 0.12 | 0.3 |
| Copolymer of acrylamide and methacrylamidopropyl trimethylammonium chloride[24] | 0.3 | 0.2 | 0.3 | 0.1 | 0.3 |
| Antifoam material of any of examples 1-14 prior to isolation of the antifoam molecule | 0.2 | 0.1 | 0.2 | 0.2 | 0.2 |
| Water, perfumes, dyes, buffers, solvents and other optional components | to 100% pH 8.0-8.2 | to 100% pH 8.0-8.2 | to 100% pH 8.0-8.2 | to 100% pH 8.0-8.2 | to 100% pH 8.0-8.2 |

Examples 17A-17G

Liquid Detergent Composition

Liquid detergent fabric care composition 17A-17G are made by mixing together the ingredients listed in the order and proportions shown[1] in Table-5. The liquid detergent fabric care composition is placed within a unit dose pouch. Such pouch comprises walls that comprise polyvinyl alcohol.

TABLE 5

| Liquid Detergent Composition examples 17A-17G | | | | | | | |
|---|---|---|---|---|---|---|---|
| Ingredient (wt %) | 17A | 17B | 17C | 17D | 17E | 17F | 17G |
| $C_{12}$-$C_{15}$ alkyl polyethoxylate (3.0) sulfate[2] | 8.5 | 2.9 | 2.9 | 2.9 | 6.8 | 9.1 | 9.1 |
| $C_{11.8}$ linear alkylbenzene sulfonic acid[6] | 11.4 | 8.2 | 8.2 | 8.2 | 1.2 | 5.7 | 5.7 |
| $C_{14}$-$C_{15}$ alkyl 7-ethoxylate[2] | — | 5.4 | 5.4 | 5.4 | 3.0 | | |
| $C_{12}$-$C_{14}$ alkyl 7-ethoxylate[19] | 7.6 | — | — | — | 1.0 | 0.2 | 0.2 |
| $C_{12}$ alkyl dimethyl amine oxide[5] | | | | | | 0.6 | 0.6 |
| 1,2 Propane diol[3] | 6.0 | 1.3 | 1.3 | 6.0 | 0.2 | 0.8 | 0.8 |
| Ethanol[3] | — | 1.3 | 1.3 | — | 1.4 | 0.7 | 0.7 |
| Diethylene Glycol[3] | 4.0 | — | — | — | | | |
| Na Cumene Sulfonate[27] | — | 1.0 | 1.0 | 0.9 | — | 1.1 | 3.1 |
| $Cu_{12}$-$C_{18}$ Fatty Acid[5] | 9.5 | 3.5 | 3.5 | 3.5 | 4.5 | 0.7 | 0.7 |
| Citric acid[20] | 2.8 | 3.4 | 3.4 | 3.4 | 2.4 | 2.1 | 2.1 |
| Protease (40.6 mg/g/)[7] | 1.0 | 0.6 | 0.6 | 0.6 | 0.3 | | |
| Protease (54.5 mg/g/)[7] | | | | | | 0.3 | 0.3 |
| Amylase, Natalase 200 L (29.26 mg/g)[25] | — | 0.1 | 0.1 | 0.1 | — | | |
| Amylase, Termamyl Ultra (25.1 mg/g)[25] | 0.7 | 0.1 | 0.1 | 0.1 | 0.1 | 0.1 | 0.1 |
| Mannanase, Mannaway 25 L (25 mg/g)[25] | 0.1 | 0.1 | 0.1 | 0.1 | 0.02 | | |
| Xyloglucanase, Whitezyme (20 mg/g)[25] | 0.2 | 0.1 | 0.1 | 0.1 | — | | |
| Fluorescent Whitening Agent[4] | 0.2 | 0.1 | 0.1 | 0.1 | — | 0.04 | 0.04 |
| Diethylene triamine pentamethylene phosphonic acid[3] | — | 0.3 | 0.3 | 0.3 | 0.1 | | |
| Diethylenetriamine pentaacetic acid[3] | | | | | | 0.4 | 0.4 |
| Hydroxy Ethylidene 1,1 Di Phosphonic acid | 1.5 | — | — | — | — | | |

TABLE 5-continued

Liquid Detergent Composition examples 17A-17G

| Ingredient (wt %) | 17A | 17B | 17C | 17D | 17E | 17F | 17G |
|---|---|---|---|---|---|---|---|
| Zwitterionic ethoxylated quaternized sulfated hexamethylene diamine[23] | 2.1 | 1.0 | 1.0 | 1.0 | 0.7 | — | — |
| Grease Cleaning Alkoxylated Polyalkylenimine Polymer[22] | — | 0.4 | 0.4 | 0.4 | — | — | 1.5 |
| Ethoxylated polyamine[21] | — | — | — | — | — | 2.2 | — |
| PEG-PVAc Polymer[26] | 0.9 | 0.5 | 0.5 | 0.5 | — | — | — |
| Hydrogenated castor oil[10] | 0.8 | 0.4 | 0.4 | 0.4 | 0.3 | 0.15 | 0.15 |
| Sodium tetraborate[3] | — | 1.3 | — | — | 1.2 | 1.1 | 1.1 |
| 4 Formyl phenyl boronic acid | — | — | 0.025 | — | — | — | — |
| Antifoam material of any of examples 1-14 prior to isolation of the antifoam molecule | 0.4 | 0.3 | 0.3 | 0.2 | 0.3 | 0.15 | 0.15 |
| Tinosan ® HP 100 via BASF | — | — | — | — | — | 0.05 | 0.05 |
| Solvents, perfumes, dyes, buffers, neutralizers, stabilizers and other optional components | to 100% pH 8.0-8.2 | to 100% pH 8.0-8.2 | to 100% pH 8.0-8.2 | to 100% pH 8.0-8.2 | to 100% pH 8.0-8.2 | to 100% pH 8.0-8.5 | to 100% pH 8.0-8.5 |

[1] An appropriately sized container is used to contain the mixture. Mixing is done using an IKA RW 20D 51 overhead mixer, model RW20D-S1 and a R 1345 four-bladed propeller stirrer, 10 cm head diameter, from VWR Randor, Pennsylvania, VWR order catalog number 33994-112.
[2] Available from Shell Chemicals, Houston, TX.
[3] Available from Sigma Aldrich Chemicals, Milwaukee, WI
[4] Available from Ciba Specialty Chemicals, High Point, NC
[5] Available from P&G Chemicals, Cincinnati, OH
[6] Available from Huntsman Chemicals, Salt Lake City, UT.
[7] Available from DuPont Industrial Biosciences, South San Fancisco, CA.
[10] Available under the tradename ThixinR from Elementis Specialties, Highstown, NJ
[18] Available from Evonik Corporation, Hopewell, VA.
[19] Available from Sasol Chemicals, Johannesburg, South Africa.
[20] Available from Genencor International, South San Francisco, CA.
[21] 600 g/mol molecular weight polyethylenimine core with 20 ethoxylate groups per —NH and available from BASF (Ludwigshafen, Germany)
[22] Described in WO 01/05874 and available from BASF (Ludwigshafen, Germany)
[23] 600 g/mol molecular weight polyethylenimine core with 24 ethoxylate groups per —NH and 16 propoxylate groups per —NH. Available from BASF (Ludwigshafen, Germany).
[24] Available from Nalco Chemicals, Naperville, IL.
[25] Available from Novozymes, Copenhagen, Denmark.
[26] PEG-PVA graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units. Available from BASF (Ludwigshafen, Germany).
[27] Availavle from Huntsman Holland, Saint-Mihiel, France Examples 18A-18D Rinse-Added Fabric Care Compositions Rinse-Added fabric care compositions 18A -18D are prepared by mixing together ingredients shown below in Table-6:

TABLE 6

Rinse-Added Fabric Care Composition examples 18A-18D

| Ingredient | 18A | 18B | 18C | 18D |
|---|---|---|---|---|
| Fabric Softener Active[28] | 16.2 | 11.0 | 16.2 | — |
| Fabric Softener Active[29] | — | — | — | 5.0 |
| Polyethylene inline[30] | 0.25 | 0.25 | — | — |
| Quaternized polyacrylamide[31] | — | — | 0.25 | 0.25 |
| Calcium chloride[3] | 0.15 | 0. | 0.15 | — |
| Ammonium chloride[3] | 0.1 | 0.1 | 0.1 | — |
| Antifoam material of any of examples 1-14 prior to isolation of the antifoam molecule | 0.1 | 0.1 | 0.1 | 0.1 |
| Perfume[32] | 0.85 | 2.0 | 0.85 | 1.0 |
| Perfume microcapsule[17] | 0.65 | 0.75 | 0.65 | 0.3 |
| Water, suds suppressor, stabilizers, pH control agents, buffers, dyes & other optional ingredients | to 100% pH = 3.0 | to 100% pH = 3.0 | to 100% pH = 3.0 | to 100% pH = 3.0 |

[17] Available from Encapsys Inc, Appleton, WI
[28] N,N di(tallowoyloxyethyl)-N,N dimethylammonium chloride available from Evonik Corporation, Hopewell, VA.
[29] Reaction product of fatty acid with Methyldiethanolamine, quaternized with Methylchloride, resulting in a 2.5:1 molar mixture of N,N-di(tallowoyloxyethyl) N,N-dimethyl-ammonium chloride and N-(tallowoyloxyethyl) N-hydroxyethyl N,N-dimethylammonium chloride available from Evonik Corporation, Hopewell, VA.
[30] Available from Nippon Shokubai Company, Tokyo, Japan under the trade name Epomin ® 1050.
[31] Cationic polyacrylamide polymer such as a copolymer of acrylamide-co-[2-(acryloylamino)ethyl]tri-methylammonium chloride (quaternized dimethyl aminoethyl acrylate) available from BASF, AG, Ludwigshafen under the trade name Rheovis CDE.
[32] International Flavors and Fragrances, New York, New York The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A molecule having the formula $$[R_1R_2R_3SiO_{1/2}]_{(j+2l+2)}[R_4R_5SiO_{2/2}]_m[R_6SiO_{3/2}]_j[SiO_{4/2}]_l$$

wherein:
a) j is an integer from 0 to 150;
b) m is an integer from 0 to 1500;
c) l is an integer from 0 to 150, preferably from 0 to 150;
with the provisio j+m+l equals an integer greater than or equal to 1 and at least one of the moieties $R_1$ through $R_6$=X—Z;
d) each of $R_1$, $R_2$, $R_3$, $R_4$, $R_5$ and $R_6$ moiety is independently selected from the group consisting of H, OH, $C_1$-$C_{32}$ alkyl, $C_1$-$C_{32}$ substituted alkyl, $C_6$-$C_{32}$ aryl, $C_5$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy and X—Z, preferably each $R_{1-6}$ is independently selected from the group consisting of OH, $C_1$-$C_{12}$ alkyl, $C_1$-$C_{12}$ substituted alkoxy, $C_1$-$C_{12}$ substituted alkoxy and X—Z;
e) each X is oxygen and
f) each Z is silica moiety, preferably said silica moiety is an agglomerate, preferably said particle or agglomerate has a particle size (d50) from about 0.1 microns to about 250 microns;
wherein said silica comprises a moiety selected from the group consisting of
—OSi($R_7$)$_3$ wherein for said —OSi($R_7$)$_3$ each $R_7$ is independently $C_1$-$C_{22}$ alkyl group and/or $C_1$-$C_{22}$ substituted alkyl; —OH; and mixtures thereof.

2. A molecule according to claim 1 wherein at least one of $R_1$, $R_2$, $R_3$, $R_4$, $R_5$ and $R_6$ moieties comprise an aryl group.

3. A molecule according to claim 1 wherein said silica is selected from the group consisting of natural $SiO_2$ nanoparticles, synthetic $SiO_2$ nanoparticles and mixtures thereof.

4. A composition comprising, based on total composition weight:
a) from about 2% to about 90% of a surfactant;
b) from about 0.1% to about 5% of an organic material having a molecular weight of from about 30 Da to about 350 Da, said material comprising one or more of the following moieties:
(i) an aromatic moiety;
(ii) a cyclo aliphatic moiety; and
(iii) a non-cyclic aliphatic moiety comprising 1 to 10 methylene moieties, with the proviso that when said number of methylene moieties is greater than 1, said methylene moieties are uninterrupted, said non-cyclic aliphatic moiety being branched and/or comprising one or more double bonds,
with the provisos that said material does not comprise a siloxane moiety, and when said material comprises a non-cyclic aliphatic moiety but not an aromatic moiety and/or cyclo aliphatic moiety, said material has a logP of from about 2.0 to about 8.0;
c) a carrier, preferably the carrier comprises water and/or a water soluble solvent; and
d) from about 0.0001% to about 5%, a molecule selected from the group consisting of the molecules of claim 1, and combinations thereof.

5. A composition according to claim 4 further comprising:
a) from about 0.001% to about 5% an organomodified silicone comprising units of the following formula(I):

$$R_a(RO)_bR_cSiO_{(4-a-b-c)/2} \quad \text{Formula (I)}$$

wherein:
each R is independently selected from the group consisting of H, an aromatic hydrocarbon radical covalently attached to silicon via an aliphatic group, a monovalent, optionally substituted, aromatic hydrocarbon radical which is attached to the silicon atom via a carbon ring atom and a monovalent, SiC-bonded, optionally substituted, aliphatic hydrocarbon radical that optionally comprises a heteroatom;
the index a is 0, 1, 2 or 3;
the index b is 0, 1, 2 or 3;
the index c is 0, 1, 2 or 3 with the proviso that:
for each of said Formula I units, the sum of indices a, b, and c is less than or equal to 3;
1% to 100% of said Formula (I) units, have an index c that is not 0;
for at least 50% of said Formula I units the sum of indices a, b, and c is 2; and
the sum of the mole percentage of R moieties in said organomodified silicone that are aromatic hydrocarbon radicals covalently attached to silicon via an aliphatic group, and/or a monovalent, optionally substituted, aromatic hydrocarbon radical which is attached to the silicon atom via a carbon ring atom is from about 1 mole percent to about 75 mole percent; and
b) an optional solvent.

6. A composition according to claim 4 wherein from about 1 to about 75 mole percent of said organomodified silicone's R moieties are selected from the group consisting of 2-phenylpropyl moieties and/or phenyl moieties.

7. A composition according to claim 4 further comprising from about 0.001% to about 5% a silicone resin comprising units of the following formula(II):

$$R^3_d(R^4O)_eSiO_{(4-d-e)/2} \quad \text{Formula (II)}$$

wherein:
a) each $R^3$ is independently selected from H, a monovalent, SiC-bonded, optionally substituted, aliphatic hydrocarbon radical that optionally comprises a heteroatom, or an aromatic hydrocarbon radical covalently attached to silicon via aliphatic groups;
b) each $R^4$ is independently selected from H, or a monovalent, optionally substituted aliphatic hydrocarbon radical, that optionally comprises a heteroatom;
c) the index d is 0, 1, 2 or 3; and
d) the index e is 0, 1, 2 or 3.

8. A composition according to claim 4 wherein the surfactant is selected from the group consisting of anionic surfactants, cationic surfactants, nonionic surfactants, zwitterionic surfactants, ampholytic surfactants and mixtures thereof.

9. A composition according to claim 4 wherein said organic material comprises a perfume raw material.

10. A composition according to claim 4 wherein the organic compound contains an aromatic moiety.

11. A composition according to claim 4 further comprising an adjunct ingredient selected from the group consisting of color care polymers, deposition aids, surfactant boosting polymers, pH adjusters, product color stabilizers, preservatives, solvents, builders, chelating agents, dye transfer inhibiting agents, dispersants, enzymes, and enzyme stabilizers, catalytic materials, bleach, bleach activators, polymeric dispersing agents, clay soil removal/anti-redeposition agents, brighteners, suds suppressors, dyes, UV absorbers, perfume in addition to said organic material, perfume delivery systems, structure elasticizing agents, thickeners/structurants, fabric softeners, hydrotropes, oligoamines, processing aids, hueing agents, and/or pigments.

12. A composition according to claim 4 comprising an anionic surfactant selected from the group consisting of a $C_9$-$C_{18}$ alkyl benzene sulfonate surfactant; a $C_{10}$-$C_{20}$ alkyl sulfate surfactant; a $C_{10}$-$C_{18}$ alkyl alkoxy sulfate surfactant, said $C_{10}$-$C_{18}$ alkyl alkoxy sulfate surfactant having an average degree of alkoxylation of from 1 to 30 and the alkoxy comprises a $C_1$-$C_4$ chain, and mixtures thereof.

13. A composition according to claim 4 further comprising a fabric softener active.

14. A composition according to claim 13 comprising wherein fabric softener active comprises one or more ester quats.

15. A method of treating and/or cleaning a situs, said method comprising
 a) optionally washing, rinsing and/or drying said situs;
 b) acting said situs with a molecule according to claim 1; and
 c) optionally washing, rinsing, and/or drying said situs.

* * * * *